US011541120B2

(12) United States Patent
Kalaritis

(10) Patent No.: US 11,541,120 B2
(45) Date of Patent: Jan. 3, 2023

(54) PHOSPHONIUM-BASED IONIC DRUG CONJUGATES

(71) Applicant: Anthos Partners, LP, Austin, TX (US)

(72) Inventor: Panos Kalaritis, Austin, TX (US)

(73) Assignee: Anthos Partners, LP, Austin, TX (US)

( * ) Notice: Subject to any disclaimer, the term of this patent is extended or adjusted under 35 U.S.C. 154(b) by 0 days.

(21) Appl. No.: 16/770,318

(22) PCT Filed: Dec. 5, 2018

(86) PCT No.: PCT/US2018/064072
§ 371 (c)(1),
(2) Date: Jun. 5, 2020

(87) PCT Pub. No.: WO2019/113210
PCT Pub. Date: Jun. 13, 2019

(65) Prior Publication Data
US 2020/0353087 A1    Nov. 12, 2020

Related U.S. Application Data

(60) Provisional application No. 62/594,826, filed on Dec. 5, 2017.

(51) Int. Cl.
| | | |
|---|---|---|
| A61K 47/54 | (2017.01) | |
| A61K 31/192 | (2006.01) | |
| A61K 31/197 | (2006.01) | |
| A61K 31/375 | (2006.01) | |
| A61K 31/401 | (2006.01) | |
| A61K 31/47 | (2006.01) | |
| A61K 31/575 | (2006.01) | |
| A61K 31/655 | (2006.01) | |

(52) U.S. Cl.
CPC .......... *A61K 47/541* (2017.08); *A61K 31/192* (2013.01); *A61K 31/197* (2013.01); *A61K 31/375* (2013.01); *A61K 31/401* (2013.01); *A61K 31/47* (2013.01); *A61K 31/575* (2013.01); *A61K 31/655* (2013.01)

(58) Field of Classification Search
CPC .............. A61K 47/5541; A61K 31/192; A61K 31/197; A61K 31/375; A61K 31/401; A61K 31/47; A61K 31/575; A61K 31/655
See application file for complete search history.

(56) References Cited

U.S. PATENT DOCUMENTS

| | | |
|---|---|---|
| 3,341,580 A | 9/1967 | Hechenbleikner |
| 4,014,918 A | 3/1977 | Martel |
| 4,049,648 A | 9/1977 | Bundy |
| 4,266,079 A | 5/1981 | Doorakian et al. |
| 4,405,766 A | 9/1983 | Bertram et al. |
| 4,774,011 A | 9/1988 | Mori et al. |
| 4,892,944 A | 1/1990 | Mori et al. |
| 4,911,928 A | 3/1990 | Wallach |
| 4,931,563 A | 6/1990 | Madison et al. |
| 5,578,694 A | 11/1996 | Yokoyama et al. |
| 5,628,984 A | 5/1997 | Boucher, Jr. |
| 5,834,014 A | 11/1998 | Weiner et al. |
| 6,183,830 B1 | 2/2001 | Okamoto et al. |
| 6,919,372 B1 | 7/2005 | Yamashita et al. |
| 7,232,809 B2* | 6/2007 | Murphy ................. A61K 31/66 514/100 |
| 8,349,902 B2 | 1/2013 | Skulachev et al. |
| 9,365,596 B2 | 6/2016 | Zheng et al. |
| 9,408,859 B2 | 8/2016 | Skulachev et al. |
| 10,085,966 B2* | 10/2018 | Murphy ................. A61P 17/10 |
| 2010/0297262 A1* | 11/2010 | Basu .................... A61K 31/353 514/459 |
| 2016/0024421 A1 | 1/2016 | Qu et al. |
| 2016/0075726 A1 | 3/2016 | Neuzil et al. |
| 2017/0189429 A1* | 7/2017 | Dudley ................. A61L 29/16 |

FOREIGN PATENT DOCUMENTS

| | | |
|---|---|---|
| WO | WO 2001/074315 A2 | 10/2001 |
| WO | WO 2007/022255 A2 | 2/2007 |

OTHER PUBLICATIONS

International Search Report and Written Opinion of the International Searching Authority Corresponding to International application No. PCT/US 2018/064072 dated Mar. 22, 2019.

International Preliminary Report on Patentability Corresponding to International application No. PCT/US 2018/064072 dated Jun. 18, 2020.

Ames et al., "Oxidants, antioxidants, and the degenerative diseases of aging." Proc. Nat. Acad. Sci. USA, vol. 90, pp. 7915-7922 (1993).

Aoyagi et al., "Effective synthesis of cyclic carbonates from carbon dioxide and epoxides by phosphonium as catalysts in alcoholic solvents." Tetrahedron Letters, vol. 54, pp. 7031-7034 (2013).

Balaban et al., "Mitochondria, oxidants, and aging." Cell, vol. 120, pp. 483-495 (2005).

Banga et al., "Hydrogel-based Iontotherapeutic Delivery Devices for Transdermal Delivery of Peptide/Protein Drugs." Pharm. Res., vol. 10(5), pp. 697-702 (1993).

(Continued)

*Primary Examiner* — My-Chau T. Tran
(74) *Attorney, Agent, or Firm* — Jenkins, Wilson, Taylor & Hunt, P.A.

(57) ABSTRACT

Phosphonium-based ionic conjugates (PBICs) are described. The PBICs each include a cationic binding partner comprising a phosphonium ion and an anionic binding partner comprising a pharmaceutically active compound, or prodrug, or derivative thereof. The conjugate can have at least one enhanced physiochemical, pharmacokinetic and/or therapeutic quality as compared to the pharmaceutically active compound when not provided in a PBIC. The phosphonium-containing cationic binding partner can also serve to enhance delivery of the anionic binding partner to the cytosol and/or the inner mitochondrial space. Methods of preparing the PBICs and using the PBICs to treat disease are also described.

24 Claims, No Drawings

(56) References Cited

OTHER PUBLICATIONS

Benetollo et al., "Reaction of ketenylidenetriphenylphosphorane, PH3PC=C=O, with water: formation of methyltriphenylphosphonium hydrogencarbonate." Journal of Organometallic Chemistry, vol. 642, pp. 64-70 (2002).
Caretto et al., "Phosphonium ionic liquids (PILs) as organocatalysts for green reactions: nucleophilic electrophilic cooperative catalysis." Sciences at CA' Foscari, pp. 60-70 (2012).
Cattelan et al., "Methyltriphenylphosphonium Methylcarbonate, and All-In-One Wittig Vinylation Reagent." ChemSusChem, vol. 8, pp. 3963-3966 (2015).
Cavalli et al., "Preparation and evaluation in vitro of colloidal liposphères containing pilocarpine as ion pair." Int. J. Pharmaceutics, vol. 117, pp. 243-246 (1995).
Choi et al., "Hydrophobic ion pair formation between leuprolide and sodium oleate for sustained release from biodegradable polymeric microspheres." Int. J. Pharm., vol. 203, pp. 193-202 (2000).
Dal Pozzo et al., "New heparin complexes active by intestinal absorption: I-multiple ion pairs with basic organic compounds." Thrombosis Research, vol. 56, pp. 119-124 (1989).
Demianenko et al., "Novel Mitochondria-Targeted Antioxidants, "Skulachev-Ion" Derivatives, Accelerate Dermal Wound Healing in Animals." Biochem. (Moscow), vol. 75, pp. 274-280 (2010).
Echtay et al., "Superoxide Activates Mitochondrial Uncoupling Protein 2 from the Matrix Side" J. Biol. Chem., vol. 277(49), pp. 47129-47135 (2002).
Ferry, "Theoretical Model of Iontophoresis Utilized in Transdermal Drug Delivery." Pharmaceutical Acta Helveticae, vol. 70, pp. 279-287 (1995).
Fini et al., "Formation of ion-pairs in aqueous solutions of diclofenac salts." International Journal of Pharmaceutics, vol. 187, pp. 163-173 (1999).
Fink et al., "Bioenergetic Effects of Mitochondrial-Targeted Coenzyme Q Analogs in Endothelial Cells." The Journal of Pharmacology and Experimental Therapeutics, vol. 342(3), pp. 709-719 (2012).
Gangarosa et al., "Modem Iontophoresis for Local Drug Delivery." Int. J. Pharm., vol. 123, pp. 159-171 (1995).
Gioscia-Ryan et al., "Mitochondria-targeted antioxidant (MitoQ) ameliorates age-related arterial endothelial dysfunction in mice." J. Physiol. Vol. 592, pp. 2549-2561 (2014).
Green et al., "Iontophoretic Delivery of a Series of Tripeptides Across the Skin in vitro." Pharm. Res., vol. 8, pp. 1121-1127 (1991).
Green et al., "The Pathophysiology of Mitochondrial Cell Death." Science, vol. 305, pp. 626-629 (2004).
Jadoul et al., "Quantification and Localization of Fentanyl and TRH Delivered by Iontophoresis in the Skin." Int. J. Pharm., vol. 120, pp. 221-228 (1995).
James et al., "Archives of Biochemistry and Biophysics." Arch. Biochem. Biophys., vol. 423, pp. 47-56 (2004).
Kim et al., "Facile Synthesis of Phosphonium Slats Containing Carboxylic Acid Functional Group." Bull. Korean Chem. Soc., vol. 22(4), pp. 351-352 (2001).
Kroemer et al., "Mitochondrial control of apoptosis." Immunol. Today, vol. 18, pp. 44-51 (1997).
Lemasters et al., "The mitochondrial permeability transition in cell death: a common mechanism in necrosis, apoptosis and autophagy." Biochim. Biophys. Acta, vol. 1366, pp. 177-196 (1998).
Matschiner et al., "Optimization of Topical Erythromycin Formulations by Ion Pairing." Skin Pharmacol., vol. 8, pp. 319-325 (1995).
Miller et al., "Enabling the Intestinal Absorption of Highly Polar Antiviral Agents: Ion-Pair Facilitated Membrane Permeation of Zanamivir Heptyl Ester and Guanidino Oseltamivir." Mol. Pharm., vol. 7(4), pp. 1223-1234 (2010).
Murphy et al., "Drug delivery to mitochondria: the key to mitochondrial medicine." Adv. Drug Del. Rev., vol. 41, pp. 235-250 (2000).
Murphy, "How mitochondria produce reactive oxygen species." Biochem. J., vol. 417, pp. 1-13 (2009).
O'Brien et al., "Acyclovir: An Updated Review of its Antiviral Activity, Pharmacokinetic Properties and Therapeutic Efficacy." Drugs, vol. 37, pp. 233-309 (1989).

Obukhova et al., "Mitochondria-targeted antioxidant SkQ1 inhibits age-dependent involution of the thymus in normal and senescence-prone rats." Aging (Albany NY), vol. 1(4), pp. 389-401 (2009).
Parry et al., "Acyclovir Bioavailability in Human Skin." J. Invest. Dermatol., vol. 98(6), pp. 856-863 (1992).
Rao et al., "Reverse Iontophoresis: Noninvasive Glucose Monitoring in vivo in Humans." Pharm. Res., vol. 12(12), pp. 1869-1873 (1995).
Richter et al., "Normal oxidative damage to mitochondrial and nuclear DNA is extensive." Proc. Nat. Acad. Sci. USA, vol. 85(17), pp. 6465-6467 (1988).
Roginsky et al., "Chain-breaking antioxidant activity of reduced forms of mitochondria-targeted quinones, a novel type of geroprotectors." Aging (Albany NY), vol. 1 (5), pp. 481-489 (2009).
Russell et al., "Synthesis of new water-soluble phosphonium salts and their Wittig reactions in water." J. Chem. Soc., Perkin Trans., vol. 1, pp. 505-513 (2000).
Santi et al., "Drug Reservoir Composition and Transport of Salmon Calcitonin in Transdermal Iontophoresis." Pharm. Res., vol. 14(1), pp. 63-66 (1997).
Santi et al., "Reverse Iontophoresis—Parameters Determining Electroosmotic Flow: I. pH and Ionic Strength." J. Control. Release, vol. 38, pp. 159-165 (1996).
Santi et al., "Reverse Iontophoresis—Parameters Determining Electroosmotic Flow: II. Electrode Chamber Formulation." J. Control. Release, vol. 42, pp. 29-36 (1996).
Saraste, "Oxidative Phosphorylation at the fin de siècle." Science, vol. 283, pp. 1488-1493 (1999).
Sarveyia et al., "Ion-pairs of ibuprofen: increased membrane diffusion." Journal of Pharmacy and Pharmacology, vol. 56(6), pp. 717-724 (2004).
Shigenaga et al., "Oxidative damage and mitochondrial decay in aging." PNAS, vol. 91(23), p. 10771-10778 (1994).
Sineerat et al., "Ion Pair Complex for Drug Delivery System." Isan. J. Pharm. Sci., vol. 4, pp. 140-150 (2008).
Skulachev et al., "An attempt to prevent senescence: A mitochondrial approach." Biochim. Biophys. Acta, vol. 1787, pp. 437-461 (2009).
Skulachev, "Prevention of cardiolipin oxidation and fatty acid cycling as two antioxidant mechanisms of cationic derivatives of plastoquinone (SkQs)." vol. 1797, pp. 878-889 (2010).
Smith et al., "Mitochondria-Targeted Antioxidants in the Treatment of Disease." Ann. NY Acad. Sci., vol. 1147, pp. 105-111 (2008).
Smith et al., "Targeting Coenzyme Q Derivatives to Mitochondria." Meth. Enzymol., vol. 382, pp. 45-67 (2004).
Suresh et al., "Ion-paired Drug Delivery: An Avenue for Bioavailability Improvement." Sierra Leone Journal of Biomedical Research, vol. 3(2), pp. 70-76 (2011).
Sznitowska et al., "Increased partitioning of pilocarpine to the oily phase of submicron emulsion does not result in improved ocular bioavailability." Int. J. Pharmaceutics, vol. 202, pp. 161-164 (2000).
Tan et al., "The Enhancing Effect of Ion-pairing on the Skin Permeation of Glipizide." AAPS PharmSciTech, vol. 10(3), pp. 967-976 (2009).
Thysman et al., "Human Calcitonin Delivery in Rats by Iontophoresis." J. Pharm. Pharmacol., vol. 46, pp. 725-730 (1994).
Trotta et al., "Influence of ion pairing on topical delivery of retinoic acid from microemulsions." J. Control Release, vol. 86, pp. 315-321 (2003).
Volpato et al., "Iontophoresis Enchances the Transport of Acyclovir through Nude Mouse Skin by Electrorepulsion and Electroosmosis." Pharm. Res., vol. 12(11), pp. 1623-1627 (1995).
Wallace, "Mitochondrial Diseases in Man and Mouse." Science, vol. 283, pp. 1482-1488 (1999).
Xu et al., "Unprecedented Ring Transformation of an α, α'-Monosubstituted 2,4,5-Triphenylpyrylium Salt with η3-Phosphines: Efficient Synthesis of Aryl- and Alkylphosphonium Triphenylcyclopentadienylides." Organometallics, vol. 29, pp. 6744-6748 (2010).
Zara et al., "Pharmacokinetics of Doxorubicin Incorporated in Solid Lipid Nanospheres (SLN)." Pharmacol Res., vol. 40(3), pp. 281-286 (1999).

(56) References Cited

OTHER PUBLICATIONS

Zhang et al., "An Improved Preparation Method of Benzyl and Thenyl Triphenylphosphonium Salts." Synthetic Communications, vol. 26(16), pp. 3091-3095 (1996).

* cited by examiner

PHOSPHONIUM-BASED IONIC DRUG CONJUGATES

RELATED APPLICATIONS

This application is a national stage filing of PCT International Application No. PCT/US2018/064072, filed Dec. 5, 2018, incorporated herein by reference in its entirety, which is based on and claims the benefit of U.S. Provisional Patent Application Ser. No. 62/594,826, filed Dec. 5, 2017; the disclosure of which is incorporated herein by reference in its entirety.

TECHNICAL FIELD

The presently disclosed subject matter relates to phosphonium-based ionic conjugates (PBICs) of pharmaceutically active agents, such as commercial drugs, as well as to pharmaceutical compositions of the conjugates, and to methods of treating diseases with the conjugates. The PBICs of the pharmaceutically active agent can have at least one enhanced physicochemical, pharmacokinetic and/or therapeutic quality, such as water solubility, hydrophilicity/hydrophobicity, permeability, absoption and/or bioavailability, in comparison to the parent non-conjugated pharmaceutically active agent. Additionally, the phosphonium conjugate partner in the PBICs of the pharmaceutically active agent can act as a delivery vehicle to deliver the pharmaceutically active agent to the cytosol and, preferably, to the inner mitochondrial space. Thus, in one aspect, the presently disclosed subject matter provides a method of enhancing the pharmaceutical and/or pharmacological properties of a pharmaceutically active agent.

BACKGROUND

The development of new molecular entities for the treatment of diseases has become increasingly complex and expensive. The probability of success is typically low and the time for development very long, leaving large numbers of patients without potential remedy for extended periods of time. A significant number of drugs and drug candidates have disadvantages relating to their physiochemical properties, their pharmacokinetics, or their bioavailability that reduce their effectiveness. Such disadvantages include, for example, lack of or low solubility. This can affect the ability to formulation these drugs and drug candidates, and/or result in low absorption rates from various sites of administration, poor bioavailabilty, lack of dose proportionality, poor stability, poor penetration of the blood/brain barrier, excessive first-pass metabolism, excessive enterohepatic recirculation, ineffective compound resease at the site of action, and dose-related side effects.

Accordingly, there is an ongoing need in the art for methods of improving the physiochemical properties, pharmacokinetic properties, and/or bioavailability of a wide range of pharmaceutically active substances. In particular, there is an ongoing need for more effective pharmaceutical agents with improved therapeutic profiles.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned: likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a composition comprising an ionic conjugate comprising (a) one or more cationic compounds, wherein each cationic compound comprises a phosphonium group, and (b) an anionic compound comprising a pharmaceutically active compound or a prodrug or derivative thereof. In some embodiments, the ionic conjugate has a structure of Formula (I):

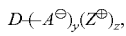

wherein: D is a residue, optionally a mono- or di-valent residue, of a pharmaceutically active compound, or a prodrug, or a derivative thereof, y is an integer, optionally wherein y is 1 or 2, each $A^{\ominus}$ is an anionic functional moiety, such that $D\text{-}(A^{\ominus})_y$ comprises a pharmaceutically active compound comprising one or more anionic moieties, an anionic form of a pharmaceutically active compound comprising one or more groups capable of forming an anion, a prodrug of a pharmaceutically active compound comprising one or more anionic moieties, an anionic form of a prodrug of a pharmaceutically active compound comprising one or more groups capable of forming an anion, a derivative of a pharmaceutically active compound wherein the derivative comprises one or more anionic moieties, or an anionic form of a derivative of a pharmaceutically active compound comprising one or more groups capable of forming an anion, optionally wherein each $A^{\ominus}$ is the anionic form of a moiety selected from the group comprising a carboxylic acid, a sulfonic acid, a phosphonic acid, an amidine, a boronic acid, a hydroxamic acid, a thiol, a phenol, and a hydroxyl; z is an integer, optionally wherein z is 1 or 2; and each $Z^{\oplus}$ is a compound comprising a phosphonium group, optionally wherein $Z^{\oplus}$ is a compound of the Formula (II):

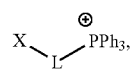

wherein L is an alkylene group, optionally a saturated or unsaturated, substituted or unsubstituted $C_1$-$C_{15}$ alkylene group; and X is H or a monovalent residue of a compound having antioxidant properties, or a reduced and/or oxidized derivative thereof, optionally wherein the compound comprising antioxidant properties is selected from the group comprising a quinone, a quinol, a benzoquinone, a benzoquinol, a plastoquinone, a plastoquinol, a chroman, a chromene, a chromone, and ascorbic acid.

In some embodiments, X has a structure of one of the Formulas (i), (ii), or (iii):

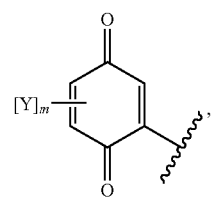

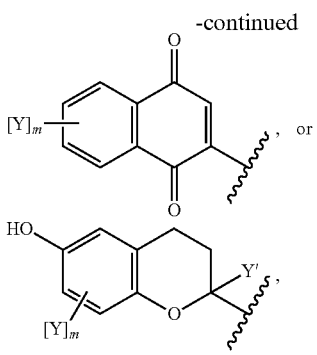

wherein: m is an integer between 0 and 3, optionally wherein m is 1, 2, or 3; each Y is independently selected from alkyl and alkoxy; and Y' is selected from H and alkyl. In some embodiments, X has a structure:

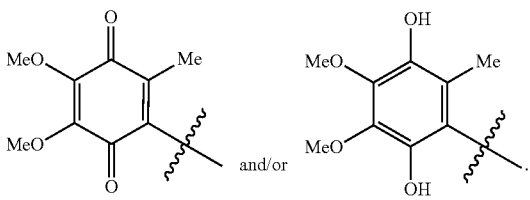 [SMILES: *C1=C(C)C(=O)C(OC)=C(OC)C1=O ; *c1c(C)c(O)c(OC)c(OC)c1O]

In some embodiments, X has a structure:

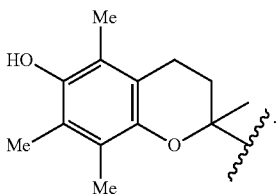

In some embodiments, the pharmaceutically active compound is a compound for treating a disease, disorder, or condition selected from the group comprising cancer; a disease, disorder, or condition associated with aging; a neurodegenerative disease, disorder or condition; sepsis; a hepatic disease, disorder or condition; a kidney disease, disorder or condition; a cardiovascular disease, disorder, or condition; diabetes or a related condition; Duchenne muscular dystrophy; a pulmonary disease, disorder, or condition; arthritis; inflammation or an inflammatory disease or disorder; an immune system disease, disorder, or condition; an eye disease, disorder, or condition; an infection; pain; a central nervous system disease, disorder or condition; a gastrointestinal disease, disorder or condition; obesity; a sleep disorder; a metabolic disorder; a dermatologic disease, disorder, or condition; a wound, disease, disorder or condition relating to hair loss; a circulatory disease, disorder, or condition; osteoporosis; blood clotting; organ transplantation; fever; and a nutritional disease, disorder or condition.

In some embodiments, the pharmaceutically active compound is selected from the group comprising fexofenadine; dabigatran; tirofiban; sulfasalazine; alitretinoin; azacytidine; bendamustine; bexarotene; bortezomib; chlorambucil; cladribine; clofarabine; cytarabine; decitabine; floxuridine; fludarabine; gemcitabine; isotretinoin; melphalan; mercaptopurine; methotrexate; panobinostat; pazopanib; pemetrexed; raltitrexed; tam ibarotene; tretinoin; vinblastine; vincristine; vinflunine; vinorelbine; vorinostat; atorvastatin; rosuvastatin; pravastatin; niacin; fluvastatin; fenofibrate; sumatriptan; baclofen; repaglinide; nateglinide; amphotericin B; valproate; esmolol; eplerenone; clopidogrel acid; valsartan; trandolapril; telmisartan; ram ipril; quinapril; perindopril; nisoldipine; nimodipine; nicardipine; moexipril; lisinopril; isradipine; fosinopril; eprosartan; enalapril; cerivastatin; captopril; benazepril; amlodipine; a qunilone antibacterial; chloramphenicol; cefditoren; celecoxib; naproxen; ketorolac; ketoprofen; ibuprofen; fenoprofen; diclofenac; penicillamine; pregabalin; gabapentin; levodopa; carbidopa; clorazepic acid; a selective thyroid hormone modulator; a prostaglandin, a prostacyclin; setipiprant, timapiprant; elvitegravir; emtricitabine; oseltamivir; tenofovir; sofosbuvir; zidovudine; zalcitabine; ganciclovir; adefovir; robenacoxib; risedronic acid; tranexamic acid; tenofovir acid; minocycline; ursodeoxycholic acid; chenodeoxycholic acid; hyodeoxycholic acid; obeticholic acid; doxorubicin; a histone deacylase inhibitor; a prostacyclin receptor (IP receptor) antagonist; a selexipag active metabolite; curcumin; squalamine; pantothenic acid; biotin; and folic acid.

In some embodiments, the pharmaceutically active compound is selected from the group comprising prostaglandin acid, prostacyclin acid, or an analog thereof; a statin; a retinoid; an angiotensin receptor blocker; a vasodialator; a dopa decarboxylase inhibitor; an anti-cancer agent; a non-steroidal anti-inflammatory drug (NSAID); a central nervous system (CNS) agent; a cholesterol lowering agent; a diabetes treatment agent; a hypertension treatment agent; a quinolone antibacterial; an osteoporosis drug; and a neuropathic pain agent.

In some embodiments, the pharmaceutically active compound, prodrug, or derivative thereof comprises one or more anionic moieties derived from a carboxylic acid, a sulfonic acid, a phosphonic acid, a boronic acid, a hydroxamic acid, or a hydroxyl group, optionally wherein each of the one or more anionic moieties is derived from a carboxylic acid.

In some embodiments, the presently disclosed subject matter provides a pharmaceutical, veterinary, or cosmetic formulation comprising the presently disclosed composition and a pharmaceutically acceptable carrier.

In some embodiments, the presently disclosed subject matter provides a method of treating a disease, disorder, or condition in a subject in need of treatment thereof, the method comprising administering to the subject a composition of the presently disclosed subject matter or a pharmaceutical, veterinary, or cosmetic formulation comprising such a composition. In some embodiments, the disease, disorder, or condition is selected from the group comprising cancer; a disease, disorder, or condition associated with aging; a neurodegenerative disease, disorder or condition; sepsis; a kidney disease, disorder or condition; a hepatic disease, disorder or condition; a cardiovascular disease, disorder, or condition; diabetes or a related condition; Duchenne muscular dystrophy; a pulmonary disease, disorder, or condition; arthritis; inflammation or an inflammatory disease or disorder; an immune system disease, disorder, or condition; an eye disease, disorder, or condition; an infection; pain; a central nervous system disease, disorder or condition; a gastrointestinal disease, disorder or condition; obesity; a sleep disorder; a metabolic disorder; a dermatologic disease, disorder, or condition; a wound, disease, disorder or condition relating to hair loss; a circulatory disease, disorder, or condition; osteoporosis; blood clotting; organ transplantation; fever; and a nutritional disease, disorder or condition. In some embodiments, the administrating is via a route selected from the group comprising oral, intravenous, subcutaneous, intramuscular, transdermal, topical, sublingual, subcutaneous, buccal, rectal, intraperitoneal, intrathecal, intravitreal, intraocular, aerosol, and nasal.

In some embodiments, the presently disclosed subject matter provides a method of enhancing the pharmaceutical and/or pharmacological properties of a pharmaceutically active agent, the method comprising: (a) providing a pharmaceutically active agent, or a prodrug or derivative thereof, wherein said pharmaceutically active agent, prodrug or derivative comprises one or more anionic groups or moieties capable of forming an anionic group; and (b) contacting the pharmaceutically active agent, prodrug, or derivative with one or more compounds comprising a phosphonium group under conditions suitable to form an ionic conjugate, optionally wherein the ionic conjugate is the ionic conjugate of a composition as described herein. In some embodiments, enhancing the pharmaceutical and/or pharmacological properties comprises increasing absorption and/or bioavailability, increasing efficacy, reducing toxicity and/or side effects, improving water solubility, improving cell membrane penetration, and/or improving blood brain barrier penetration compared to the pharmaceutical and/or pharmacological properties of the pharmaceutically active agent.

In some embodiments, the compound comprising a phosphonium group has a structure of the formula:

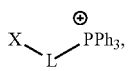

wherein L is an alkylene group, optionally a saturated or unsaturated, substituted or unsubstituted $C_1$-$C_{15}$ alkylene group; and X is a monovalent residue of a compound comprising antioxidant properties.

It is an object of the presently disclosed subject matter to provide ionic conjugates of phosphonium group-containing compounds and anionic pharmaceutically active compounds or prodrugs, or anionic derivatives thereof, pharmaceutical formulations thereof, and related treatment methods, and methods of enhancing the pharmaceutical and/or pharmacological properties of pharmaceutically active agents.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless as otherwise specifically indicated.

I. Definitions

Following long-standing patent law convention, the terms "a", "an", and "the" refer to "one or more" when used in this application, including the claims. Thus, for example, reference to "a solvent" includes mixtures of one or more solvents, two or more solvents, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, molar equivalents, time, temperature, etc. is meant to encompass in one example variations of ±20% or ±10%, in another example ±5%, in another example ±1%, and in yet another example ±0.1% from the specified amount, as such variations are appropriate to perform the disclosed methods.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. "Comprising" is a term of art used in claim language, which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl (Me), ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl (saturated or unsaturated), substituted alkyl (e.g., halo-substituted and perhalo-substituted alkyl, such as but not limited to, —CF$_3$), cycloalkyl, halo, nitro, hydroxyl, carbonyl, carboxyl, acyl, alkoxyl, aryloxyl, aralkoxyl, thioalkyl, thioaryl, thioaralkyl, amino (e.g., aminoalkyl, aminodialkyl, aminoaryl, etc.), sulfonyl, and sulfinyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, and thiophenyl.

The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to —CF$_3$), cycloalkyl, aryl, substituted aryl, aralkyl, halo, nitro, hydroxyl, acyl, carboxyl, alkoxyl, aryloxyl, aralkyloxyl, thioalkyl, thioaryl, thioaralkyl, amino (e.g., aminoalkyl, aminodialkyl, aminoaryl, etc.), sulfonyl, and sulfinyl.

In some embodiments, the term "monovalent" refers to a group that can bond (e.g., covalently bond) or is bonded to one other functional group. In some embodiments, the term "monovalent residue" refers to a derivative of a compound wherein one hydrogen atom or other single functional group (e.g., a halo or alkyl group) has been removed to provide a monovalent moiety.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

The term "arylene" refers to a bivalent aromatic group.

As used herein, the term "acyl" refers to an organic carboxylic acid group wherein the —OH of the carboxylic acid group has been replaced with another substituent. Thus, an acyl group can be represented by RC(=O)—, wherein R is an alkyl, substituted alkyl, aralkyl, substituted aralkyl, aryl or substituted aryl group as defined herein. As such, the term "acyl" specifically includes arylacyl groups, such as a phenacyl group. Specific examples of acyl groups include acetyl and benzoyl.

"Cyclic" and "cycloalkyl" refer to a non-aromatic mono- or multi-cyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" refers to an alkyl-O— group wherein alkyl is as previously described, including substituted alkyl. The term "alkoxyl" as used herein can refer to, for example, methoxyl, ethoxyl, propoxyl, isopropoxyl, butoxyl, t-butoxyl, and pentoxyl. The term "oxyalkyl" can be used interchangeably with "alkoxyl".

"Aryloxyl" refers to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to an -aryl-alkyl or -alkyl-aryl group wherein aryl and alkyl are as previously described, and can include substituted aryl and substituted alkyl. Thus, "substituted aralkyl" can refer to an aralkyl group comprising one or more alkyl or aryl group substituents. Exemplary aralkyl groups include benzyl, phenylethyl, and naphthylmethyl.

"Aralkyloxyl" or "aralkoxyl" refer to an aralkyl-O— group wherein the aralkyl group is as previously described. An exemplary aralkyloxyl group is benzyloxyl.

The term "carbonyl" refers to the group —C(=O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The term "carboxyl", "carboxylate," and "carboxylic acid" as use herein can refer refers to —C(=O)OH group. In some embodiments, "carboxyl" and "carboxylate" can also refer to the —C(=O)O$^-$ group.

The terms "halo", "halide", or "halogen" as used herein refer to fluoro, chloro, bromo, and iodo groups.

The term "hydroxyl" refers to the —OH group. The terms "phenol" or "phenolic" refer to a hydroxyl group that is directly bonded to an aromatic group (e.g., phenyl).

The term "thiol" refers to the —SH group.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl or substituted alkyl, and wherein at least one R is alkyl or substituted alkyl.

The term "phosphonium" refers to a $PR_4^+$ group or a $—R'—PR_3^+$ group, wherein each R is independently selected from H, alkyl, substituted alkyl, aralkyl, substituted aralkyl, aryl, and substituted aryl and where R' is a substituted or unsubstituted alkylene or arylene group.

The term "sulfonic acid" refers to the $—S(═O)_2OH$ group.

The term "phosphonic acid" refers to the $—P(═O)(OH)_2$ group.

The term "amidine" refers to the $—C(═NH)NH_2$ group.

The term "boronic acid" refers to the $—B(OH)_2$ group.

The term "hydroxamic acid" refers to the $—C(═O)—N(R)OH$ group, wherein R is H, alkyl, substituted alkyl, aralkyl, substituted aralkyl, aryl, or substituted aryl.

A structure represented generally by a formula such as:

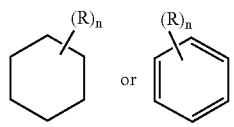

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure, replacing an H atom that would be bonded to that carbon in the absence of the R group. The presence or absence of the R group and the number of R groups is determined by the value of the integer n. Each R group, if more than one, is substituted on an available carbon of the ring structure rather than on another R group. For example, the structure:

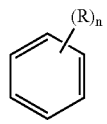

wherein n is an integer from 0 to 2 comprises compound groups including, but not limited to:

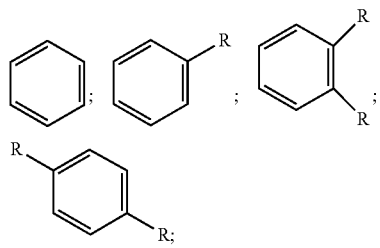

and the like.

A line crossed by a wavy line, e.g., in the structure:

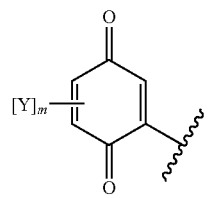

indicates the site where a substituent can bond to another group.

The terms "prostaglandin" can refer to naturally occurring 20-carbon fatty acid derivatives produced biosynthetically by the oxidative metabolism of fatty acids (e.g., arachidonic acid). In some embodiments, "prostaglandin" can also refer to analogs of the naturally occurring compounds, such as those synthetic analogs that have similar biological effects to the naturally occurring compounds and/or have been used in the pharmaceutical industry. The structures of various known classes of prostaglandins are shown, for example, in U.S. Pat. No. 4,049,648, incorporated herein by reference. As used herein, the term "analog" is meant to refer to a biologically active, modified version of a natural product, wherein one or more atoms, such as but not limited to carbon, hydrogen, oxygen, nitrogen, sulfur or a halide, have been added or subtracted from the parent structure. The term "prostanoid" refers to naturally occurring prostaglandins and prostaglandin analogs. Thus, "prostanoid" and "prostaglandin" can be used interchangeably herein. The term "prostaglandin acid" refers to a prostaglandin comprising a carboxylic acid group.

The term "pharmaceutically active compound" as used herein refers to a compound that has a desired pharmaceutical activity (e.g., that reduces the likelihood or severity of, prevents, or relieves a cause, symptom and/or side effect of a disease, disorder or condition). In some embodiments, the pharmaceutically active compound is a commercially available and/or FDA approved drug compound. In some embodiments, the pharmaceutically active compound is a compound that is undergoing clinical trials for the treatment of one or more disease, disorders or conditions or that has shown or is believed to have a desirable effect in vitro or in vivo related to the treatment and/or alleviation of a disease, disorder or condition. In some embodiments, the pharmaceutically active compound is an active metabolite of another pharmaceutically active compound.

In some embodiments, the term "derivative" as used herein in the context of a pharmaceutically active compound refers to a structurally modified pharmaceutically active compound, wherein the structure of the parent pharmaceutically active compound has been derivatized (e.g., via one or more chemical reactions) to include one or more additional chemical functional groups attached to the parent compound via one or more covalent bonds. In particular, the one or more additional chemical functional groups can include at least one anionic functional group or at least one functional group that is capable of forming an anion under certain conditions (e.g., in the presence of a certain pH or enzyme). Thus, in some embodiments, a pharmaceutically active compound that does not include an anionic functional group or a functional group that is capable of forming an anion can be derivatized to include such a group.

The term "prodrug" as used herein refers to a compound that, upon administration to a recipient, is capable of providing (directly or indirectly) a pharmaceutically active compound (e.g. a known pharmaceutically active compound) or an active metabolite or residue thereof. A prodrug can be a derivative of a pharmaceutically active compound that comprises one or more groups that are cleaveable under physiological conditions (e.g., at a certain pH or by an enzyme). Such groups include, but are not limited to, an ester, carbamate, carbonate, phosphate ester, azo group or amide. In some, but not all, embodiments, the prodrug has less pharmaceutical activity than the parent compound (i.e., the pharmaceutically active compound upon which the structure of the prodrug is based and to which the prodrug can be transformed in vivo). In some embodiments, the prodrug compound has no measurable inhibitory activity prior to transformation to the parent compound. In some embodiments, the prodrug itself has a desired pharmaceutical activity.

The terms "conjugate" and "conjugated" as used herein can refer to compositions that comprise at least two different chemical moieties or molecules (e.g., small molecules, polymers, proteins, oligonucleotides, etc.) bonded to one another, such as via ionic, coordinative or covalent bonds. Typically, a "conjugate" refers to a situation where the two entities are bonded via a single bond or linkage. The term "ionic conjugate" as used herein refers refers to a composition wherein at least two molecules are bonded to one another via one or more ionic bonds, wherein each ionic bond is an ionic bond between a cationic group on one molecule and an anionic group on another molecule.

The term "solvent" as used herein refers to a liquid that can be used to dissolve a compound or conjugate. In some embodiments, the solvent is solvent typically used in organic chemistry in reactions involving functional group transformations or to purify organic compounds.

The term "aprotic solvent" refers to a solvent molecule which can neither accept nor donate a proton. Examples of aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide, N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

II. General Considerations

Ion-pair delivery has emerged as a potential approach for enhancing the solubility of ionic molecules in non-polar solvents, augmenting protein and DNA transport, and addressing the poor bioavailability of hydrophilic drugs. See Suresh, Sierra Leone Journal of Biomedical Research 2011, 3(2): 70-76. In a study with diclofenac, for example, it was demonstrated that diclofenac ion-pairs made with organic amine cations have different permeabilities depending on the nature of the cations. See Fini et al., International Journal of Pharmaceutics 1999, 187: 163-173. They also had higher extinction coefficients, suggesting their importance in driving the formation of species that conjugate an ionic (hydrophilic) character together with an (hydrophobic) affinity towards a lipid phase. The study concluded that ion pairs can offer a better chance of absorption, with the possibility of alternative pathways and absorption mechanisms.

Matschiner and colleagues improved the lipophilicity of erythromycin with a formulation involving the ion-pair between erythromycin and octadecansulfonate. See Matschiner et al., Skin Pharmacol 1995; 8:319-325. Leuprolide acetate, an analogue of luteinizing hormone-releasing hormone, was hydrophobically ion paired with a long chain fatty acid, sodium oleate, in an aqueous solution. See Choi and Park, Int J Pharm. 2000; 203(1-2):193-202. The study indicated that ion-pairing rendered the protein more hydrophobic, increased its solubility in organic solvents, and thereby improved its loading.

In transdermal delivery, charged drug molecules do not readily partition into or permeate through human skin. Formation of lipophilic ion-pairs can increase stratum corneum penetration of charged species. The ion-pair can then dissociate in the aqueous microenvironment of the epidermis, releasing the parent charged drug, which can diffuse within the epidermal and dermal tissues. A study of ibuprofen ion pairs with amine counter ions reported a 16-fold increase in the steady-state flux of ibuprofen ion-pairs across a lipophilic membrane. See Sarveyia et al., Journal of Pharmacy and Pharmacology 2004, 56(6): 717-24. Nash and coworkers tested the ion pair absorption hypothesis with respect to the topical route of drug delivery by preparing various lidocaine-n-alkanoate ion pairs. See Nash et al., Skin Pharmacol. 1992, 5(3):160-70. To improve transdermal delivery of meloxicam, Zhang and coworkers studied ion-pair formation with organic amine bases. See Zhang et al., Drug Development and Industrial Pharmacy 2009, 35(6): 663-670. Their results indicated that the degree of enhancement depends on the structure and hydrophilicity of the counter ions. A study of glipizide ion pairs with organic amines suggested that the formation of ion-pairs between glipizide and counter ions is a useful method to promote the skin permeation of glipizide. See Tan et al., AAPS PharmSciTech 2009, 10(3): 967-976.

In ocular delivery, submicron emulsions containing pilocarpine as an ion-pair with mono-dodecylphosphoric acid have been investigated. See Sznitowska et al., Int. J Pharmaceutics 2000, 202: 161-164. Another study assessed the ion pairing of retinoic acid (R.A) with organic amines using microemulsions as delivery vehicles to influence topical permeation. See Trotta et al., J Control Release. 2003, 86(2-3): 315-21. Cavalli and coworkers have reported sustained ocular delivery of pilocarpine using aqueous dispersions of solid liposheres containing pilocarpine ion pairs with various phosphates. See Cavalli et al., Int. J. Pharmaceutics 1995, 117: 243-246.

In oral delivery, an ion-pairing approach of the low-permeability antiviral agents zanamivir heptyl ester and guanidino oseltamivir using 1-hydroxy-2-naphthoic acid enhanced the apparent permeability of both compounds across Caco-2 cell monolayers in a concentration-dependent manner. See Miller, Mol Pharm. 2010, 7(4): 1223-1234. Organic ion pairs of heparin have been used to improve its oral absorption. See Dal Pozzo et al., Thrombosis Research 1989, 56: 119-124.

In parenteral delivery, doxorubicin-containing ion-pair complexes can have enhanced lipophilicity, which can result in an increase in apparent partition coefficient between lipid and water, enabling higher drug payloads and bio-distribution. See Zara et al., Pharmacol Res. 1999, 40(3): 281-6.

In delivery by inhalation, the charged prodrug sodium isoniazid methanesulfonate has been ion paired with hydrophobic cations, such as alkyl-trimethylammonium or tetra-alkylammonium. The water solubility of the tetra-heptylammonium complex was about 220-fold lower than that of the sodium salt of isonazide. The half-life of this complex was on the order of 30 min, making the enhanced transport of the drug across biological barriers possible. See Zhou et al., J Pharm Sci. 2002, 91(6): 1502-11. A water insoluble complex of cationic propranolol HCl with anionic sodium lauryl sulfate appeared to provide promising sustained drug delivery and was capable of being encapsulated in microparticles for a more sustained drug release effect. See Sineerat et al., Isan J Pharm Sci. 2008, 4: 140-150.

Ion pair delivery strategies to date have focused primarily on organic amine counterions. Ion pairs of ionizable drugs with alkyltriphenylphosphonium cations represent a new class of molecules that can improve the delivery and therapeutic profile of commercial drugs through the alteration of their physicochemical properties. Additionally, the ability of these phosponium cations to permeate the cell membranes and their affinity to gravitate into the mitochondrial space renders them as prime candidates for targeted delivery of commercial drugs, hence the description as "ionic conjugates".

Mitochondria generate electric potential difference across their inner membrane. This renders the mitochondrial interior a unique intracellular compartment that is negatively charged relative to cytosol. Understanding of the electric potential difference across the mitochondria inner membrane led the development of triphenylphosphonium ions (TPP) as tethers that target the mitochondria. More particularly, the positive charge of the TPP ion is delocalized across the hydrophobic (phenyl) residues making TPP ions very lipophilic. This property makes TPP ions capable of penetrating hydrophobic membranes and, even beyond this, of focusing them on the negatively charged mitochondria compartment.

Mitochondria are central to oxidative phosphorylation and much of metabolism. They also play an important role in other vital biological functions, such as iron-sulfur center assembly, thermogenesis, and heme biosynthesis. See Echtay et al., J. Biol. Chem. 2002, 277(49): 47129-47135; Saraste, Science 1999, 283(5407): 1488-1493; Szewczyk and Woitczak, Pharmacological Reviews 2002, 54(1): 101-127; and Wallace, Science 1999, 283(5407): 1482-1488. They are involved in cell death by both apoptotic and necrotic pathways. See Kroemer et al., Immunol. Today 1997, 18(1): 44-51; and Lamasters et al., Biochim Biophys Acta 1998, 1366(1-2): 177-196. Hence, mitochondrial dysfunction plays important role in many diseases, such as neurodegenerative diseases, heart pathologies, inflammation, stroke, sepsis, diabetes, and others. Increased oxidative damage is considered a key factor for mitochondrial dysfunction. See Shigenaga et al., PNAS 1994, 91(23): 10771-10778; Beckman and Ames, Ann NY Acad Sci. 1998, 854: 118-127; Green and Kroemer, Science 2004, 305(5684): 626-629; and Balaban et al., Cell 2005, 120(4): 483-495. In this respect, it is believed that the mitochondrion is a major source of superoxide, a reactive chemical species, within the cell that leads to oxidative damage, mitochondrial dysfunction, and eventually cell death. See Balaban et al., Cell 2005, 120(4): 483-495; and Murphy, Biochem J. 2009, 417(1): 1-13 (dio: 10.1041/BJ20081386). Thus, efforts have been made to develop new drug candidates with anti-oxidant properties targeting the mitochondria. Many anti-oxidant agents, such as vitamin E and vitamin C, were investigated without much success, possibly because they are widely distributed in the body and not focused on mytochondria.

However, two classes of anti-oxidant molecules have been developed that have high affinity for the mitochondria through the presence of a TPP reside. The molecules also include a "warhead" moiety capable of absorbing the reactive oxidative species (ROS) in the cell. In one of the two classes, the warhead is based on ubiquinol and in the other the warhead is based on plastoquinol. In both cases, the TTP residue and the warhead residue is connected via an aliphatic chain, the length of which can be tuned to give different properties to the molecules.

The lead clinical candidates from these two classes of molecules are Mitoquinol (MitoQ) and Plastoquinonyl-decyl-triphenylphosphonium (SkQ1). See Scheme 1, below. Both have been investigated in vitro and in vivo for potential therapeutic effects. See Gioscia-Ryan et al., J. Physiol. 2014, 592(12): 2549-2561; Obukhova et al., Aging 2009, 1(4): 389-401; and Roginsky et al., Aging 2009, 1(5): 481-489. The delocalized positive charge of these lipophilic molecules enables them to permeate lipid bilayers easily and accumulate hundred-fold in the mitochondria. They are effective antioxidants by inhibiting lipid peroxidation during redox cycling of the quinol/quinone forms of the compounds. See James et al., Arch. Biochem. Biophys. 2004, 423: 47-56. The major protective reaction transfers a hydrogen atom (H) from the quinol to a lipid radical (LO2), forming LOOH and generating the semiquinone form of the MTQA. See James et al., Arch. Biochem. Biophys. 2004, 423: 47-56; and Skulachev et al., Biochemica et Biophysica Acta 2010, 1797(6-7): 878-889. The ability of mitochondria-targeted antioxidants to confer greater protection against oxidative damage in the mitochondria than untargeted cellular antioxidants is attributed to their ability to cross the mitochondrial phospholipid bilayer and eliminate ROS at the source.

Scheme 1. Structures of Mitoquinol (MitoQ) and Plastoquinonyl-decyl-triphenylphosphonium (SkQ1).

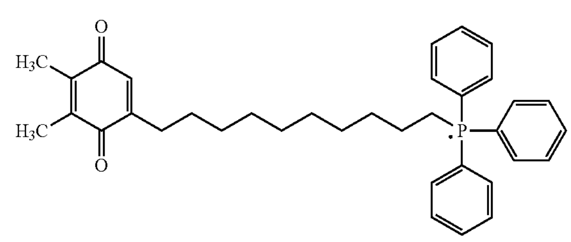

SKQ1

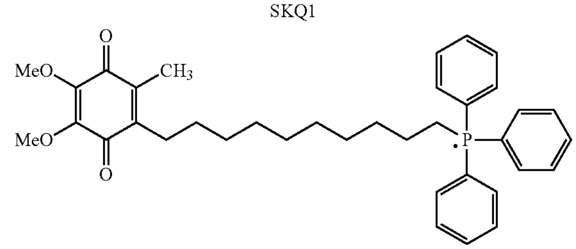

MitoQ

MitoQ (mitoquinone, mitoquinol, or a mixture of these two redox cycling compounds) includes a quinone/quinol moiety and a shortened (10 carbon or two 5-carbon prenyl units) side chain linked to a triphenylphosphonium residue that gives the molecule the ability to enter and accumulate within the mitochondria due to the electrochemical gradient. It serves as an electron carrier and an antioxidant. It reduces the production of lipid peroxide radicals within the mitochondria, thereby preventing lipid peroxidation.

SkQ1 was developed based on efforts to modify the MitoQ structure, improve the balance between antioxidant and pro-oxidant effects, and facilitate increased delivery. One modification was to convert the methoxy groups on the quinone moiety of MitoQ to methyl groups. As a result, SkQ1 demonstrated greater permeability across synthetic lipid bilayers than MitoQ. See Obukhova et al., Aging 2009, 1(4): 389-401. Several other plastoquinone based analogues of SkQ1 were made by Skulachev and coworkers, such as SkQ3 and SkQ5. Plastoquinone appears to be a better antioxidant than ubiquinone. SkQ1 penetrates hydrophobic membranes more effectively than MitoQ, is four times more hydrophobic, is more efficient than MitoQ in quenching OH radicals and other ROS in aqueous media, is four times more efficient at quenching linolate free radicals at its reduced state, and is more effective in preventing ROS-linked cell death (apoptotic or necrotic).

Despite a high level of research activity related to these compounds, commercial application of these mitochondria-targeted antioxidants has been limited thus far. SkQ1 was recently introduced as an ophthalmic product in Russia and completed a Phase II study in US. MiotQ on the other hand, completed two Phase II studies in US. The first, which targeted Parkinson's, showed no efficacy, and the second, which focused on chronic hepatitis C virus (HCV) patients, showed significant decrease in serum alanine transaminase but no effect on viral load.

But, the clinical studies associated with these molecules has revealed that TPP-containing compounds are generally safe and can be administered over extended periods of time, up to one year in the case of MitoQ at the level of 80 mg/day. Following intravenous or intraperitoneal injection in mice, MitoQ clears the plasma and substantial amounts of the compound were rapidly accumulated in the heart, brain, skeletal muscle, liver, and kidney. Extended oral administration of the compound leads to a steady-state accumulation primarily in heart, liver, and brain. Intraperitoneal injection of MitoQ leads to very rapid uptake (<5 min) of the compound into tissues creating the possibility of acute administration. MitoQ is excreted unmodified in the urine and bile and some with sulfation and glucuronidation of the ubiquinone ring. In vivo, MitoQ is in facile equilibration between the extracellular fluid, the cytosol, and the mitochondria as demonstrated by its uptake and efflux which follows the Nernstian distribution. The uptake of MitoQ is self-limiting due to its rapid reversibility and equilibration with the plasma and mitochondria membrane potentials. Triphenylmethylphosphonium (TPMP), an analogous molecule without the antioxidant warhead, showed similar characteristics and reversible uptake. It cleared the body rapidly with >90% eliminated from all organs within 24 hours with substantial amounts appearing in the urine.

The in vivo data from animal studies is consistent with a pharmacokinetic model in which orally administered TPP cations enter the bloodstream from the gut and are taken up in all tissues via non-mediated transport of the lipid bilayer of the plasma membrane, driven by the plasma membrane potential, and then enter the mitochondria membrane, driven by the large membrane potential. After several days of administration, the concentration of the cation within the mitochondria reaches a steady state distribution with the circulating blood levels, at which point the mitochondrial concentration is hundred-fold higher. At this point, the rate of absorption of the compounds matches the rate of elimination in the urine and bile. The compounds are in a dynamic equilibrium within the mitochondria that, once administration stops, the compounds re-equilibrate back into the bloodstream and eliminated rapidly. Bioavailability can also be improved by modulating lipophilicity or hydrophobicity through adjustment of the length of the linker. The derivative of MitoQ with a three carbon linker has an octanol-PBS partition coefficient of 2.8 compared to 160 for MitoQ.

Scheme 2 below shows different modifications sites on the common nucleus of the ubiquinone and plastoquinone antioxidant molecules.

Scheme 2: Modification Approaches to Quinone-based Moieties.

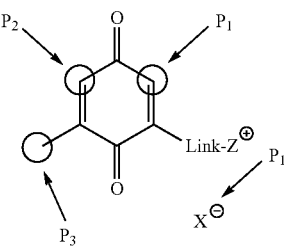

Referring to Scheme 2, based on work by the Skulachev group, P1 is a position responsible for stability and biological activity. P2 & P3: are responsible for regulation of the interaction with the mitochondrial respiratory chain. P4: is the position responsible for the penetrating activity of the biologically active substance. Finally, the linker attaching the quinone-based group to a TPP moiety $Z^+$ is a structural element that can affect the hydrophilicity of the molecule. Reducing the length of the aliphatic linker chain and increasing its hydrophilicity can improve absorption but reduces membrane penetrating ability.

III. Phosphonium-Based Ionic Conjugates

According to one aspect of the presently disclosed subject matter, the desirable properties of phosphonium-containing compounds (e.g., TPP-containing compounds) are used to improve the therapeutic profiles of pharmaceutically active compounds or the derivatives or prodrugs thereof. In some embodiments, the pharmaceutically active compound is an existing commercial pharmaceutical or another molecule with known pharmaceutical activity, such as compounds with known desirable in vitro and/or in vivo activities. In some embodiments, the pharmaceutically active compound has undesirable physiochemical properties that make, for example, formulation and/or biodelivery difficult. Driven by the plasma membrane potential, phosphonium-containing groups, such as TPP groups, can provide for the rapid cellular uptake of an associated bioactive molecule, followed by specific mitochondrial matrix accumulation.

More particularly, rather than modifying the pharmaceutically active compound (e.g., the existing pharmaceutically active compound) to covalently attach the compound to a phosphonium group, according some embodiments of the presently disclosed subject matter, a ionic conjugate is provided, wherein a cationic compound comprising a phosphonium group is non-covalently associated with the pharmaceutically active compound via ionic bonding between the phosphonium group and an anionic group on the existing pharmaceutically active compound, prodrug, or anionic derivative thereof. Accordingly, in some embodiments, ionic conjugaton can be used to improve the profiles of existing or potential drugs. The use of an ionic conjugate can provide for more rapid product development than covalent modification approaches. Covalent chemical modifications can lead to new molecules with distinct efficacy and toxicity properties that must be tested and proven again. In some embodiments, this is can be avoided by the use of ionic conjugation.

Accordingly, in some embodiments, the presently disclosed subject matter relates to the preparation of, and applications related to, phosphonium-based ionic conjugates (PBICs) that comprise an anionic compound in which the core part of the anionic compound is a proven pharmaceutically active agent or prodrug, preferably a known commercial drug, comprising or derivatized to comprise one or more anionic moieties, such as, but not limited to, an anionic form of a carboxyl, sulfonyl, hydroxamyl, boronyl, phosphatyl, or hydroxyl functionality that is conjugated ionically to at least one cationic molecule (i.e., a molecule comprising one or more cationic groups) to improve its therapeutic profile. In some embodiments, the cationic molecule is a molecule that bears a phosphonium moiety, such as, but not limited to a TPP+ moiety or another tetrasubstituted phosphorous atom. Thus, exemplary cationic molecules include, but are not limited to, TPMP, MitoQ, MitoE, SkQ1, and other related molecules. In some embodiments, the cationic molecule is other than SkQ1.

In some embodiments, the purpose of the cationic molecule is primarily to facilitate absorption, transport, and distribution of the known pharmaceutical or derivative thereof. In some embodiments, the cationic molecule can have antioxidant properties. Thus, in some embodiments, the ionic conjugate can provide a synergistic effect from the antioxidant properties of the cationic compound and the pharmaceutical properties of the anionic compound, e.g., for diseases, disorders, and conditions related to and/or involving oxidative stress.

As described above, development of the presently disclosed ionic conjugates is significantly simpler and more efficient than covalently modifying drugs to incorporate a TPP+ moiety. One advantage of the presently disclosed phosphonium-based ionic conjugates is that, unlike many other drug derivatives, the cationic compound is non-toxic, as evidenced by clinical study data related to MitoQ and SkQ1, and is excreted quickly from the body. Another advantage is that the physical properties of the cationic molecule readily permit modulation to optimize absorption and bioavailability and their in vivo attained steady state equilibrium presents an opportunity for more creative administration of drugs with serious side effects. Further, for drugs that are sensitive to oxidation, the present ionic conjugates can offer an added advantage by, in some embodiments, having an antioxidant molecule incorporated in the structure of the cationic molecule component of the conjugate.

Phosphonium-containing cationic molecules of the presently disclosed ionic conjugates can be provided by methods known in the art. For example, methods of making alkyltriphenylphosphonium molecules from halides and lower carboxylates or sulfonates are documented in the literature. Such molecules are generally produced by one of two methods: (a) via cation exchange, and/or (b) via reaction of a molecule having a good leaving group with triphenylphosphine. Phosphonium acid carboxylates and dicarboxylates have been produced previously. See U.S. Pat. No. 3,341,580, the disclosure of which is incorporated herein by reference in its entirety. Quaternary phosphonium salts of halides and lower carboxylates such as acetates and methyl carbonates, (also known as "ionic liquids") are known in the literature and have been used to catalyze certain types of chemical reactions. See A. Careto et al., Sciences at CA' Foscari 2012, 60-70. Quaternary phopsphonium salts of lower carboxylates have also been produced via the corresponding lactones. See J. N. Kim et al., Bull. Korean Chem. Soc. 2001, 22(4): 351-352.

In some embodiments, the presently disclosed subject matter provides a composition comprising an ionic conjugate comprising (a) one or more cationic compounds, which each cationic compound comprises a phosphonium group, and (b) an anionic compound comprising a pharmaceutically active compound or a prodrug or derivative thereof. In some embodiments, the pharmaceutically active compound is an active metabolite of another pharmaceutically active compound. In some embodiments, the ionic conjugate has a structure of Formula (I):

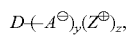

wherein:

D is a residue (e.g., a mono- or divalent residue) of a pharmaceutically active compound, or a prodrug or a derivative thereof;

y is an integer (e.g., 1 or 2);

each $A^{\ominus}$ is an anionic functional moiety, such that $D\text{-}(A^{\ominus})_y$ comprises a pharmaceutically active compound comprising one or more anionic moieties, an anionic form of a pharmaceutically active compound comprising one or more groups capable of forming an anion, a prodrug of a pharmaceutically active compound comprising one or more anionic moieties, an anionic form of a prodrug of a pharmaceutically active compound comprising one or more groups capable of forming an anion, a derivative of a pharmaceutically active compound wherein the derivative comprises one or more anionic moieties, or an anionic form of a derivative of a pharmaceutically active compound comprising one or more groups capable of forming an anion;

z is an integer (e.g., 1 or 2); and each $Z^{\oplus}$ is a compound comprising a phosphonium group.

In some embodiments, each $A^{\ominus}$ is the anionic form of a moiety that has a suitable pKa (e.g., to form an anionic group under physiological conditions), such as, but not limited to, an organic acid (e.g., a carboxylic acid, a sulfonic acid, a sulfenic acid, a boronic acid, a hydroxamic acid, a barbituric acid, an amino acid, a phosphonic acid, a phosphoric acid, etc.), a oxime, a hydroxyl, a phenol, a sulfonamide, a thiol, a uracil, a thiouracil, an amidine, and certain ketones (e.g., nitro, cyano, sulfone, and cyclic ketones). In some embodiments, each $A^{\ominus}$ is the anionic form of a moiety selected from the group comprising a carboxylic acid, a sulfonic acid, a phosphonic acid, an amidine, a boronic acid, a hydroxamic acid, a thiol, a phenol, and a hydroxyl.

In some embodiments, y and z are each 1. In some embodiments, y and z are each 2. In some embodiments, y is 2 and z is 1. Thus, for example, the ionic conjugate can comprise a mono- or di-conjugate of one or two cationic compounds (e.g., one or two TPP-containing compounds) and a dicarboxylate-containing drug compound. In some embodiments, the conjugate composition is a mixture of mono- and di-conjugates.

In some embodiments, each $Z^{\oplus}$ is a compound of Formula (II):

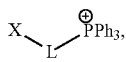

wherein L is an alkylene group and X is H or a monovalent residue of a compound having antioxidant properties, or a reduced and/or oxidized derivative thereof. In some embodiments, L is a saturated or unsaturated, substituted or unsubstituted $C_1$-$C_{15}$ alkylene group (e.g., a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkylene group). In some embodiments, L is decylene. In some embodiments, X is H. In some embodiments, X is a monovalent residue of compound having antioxidant properties, wherein the compound having antioxidant properties is selected from the group including, but not limited to, a quinone, a quinol, a benzoquinone, a benzoquinol, a plastoquinone, a plastoquinol, a chroman, a chromene, a chromone, and ascorbic acid.

In some embodiments, X has a structure of one of the Formulas (i), (ii), or (iii):

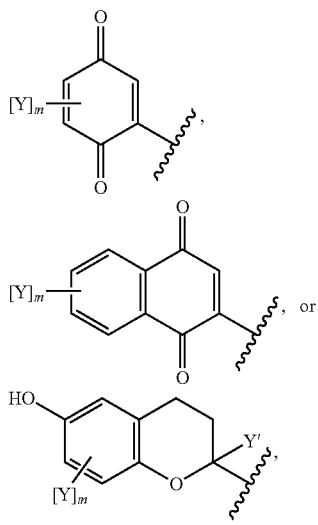

wherein: m is an integer between 0 and 3 (e.g., 0, 1, 2, or 3); each Y is independently selected from alkyl and alkoxy; and Y' is selected from H and alkyl. In some embodiments, m is 1, 2, or 3. In some embodiments, Y is $C_1$-$C_8$ alkyl or alkoxy (e.g., methyl, ethyl, propyl, butyl, pentyl, hexyl, heptyl, or octyl). In some embodiments, Y is methyl or methoxy. In some embodiments, Y' is H.

In some embodiments, X has a structure:

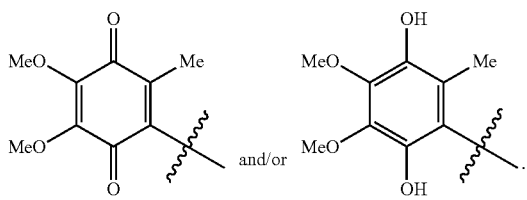 [SMILES: *C1=C(C)C(=O)C(OC)=C(OC)C1=O ; *c1c(C)c(O)c(OC)c(OC)c1O]

In some embodiments, X has a structure:

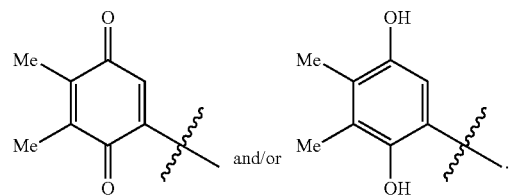 [SMILES: *C1=CC(=O)C(C)=C(C)C1=O ; *c1cc(O)c(C)c(C)c1O]

In some embodiments, X has a structure:

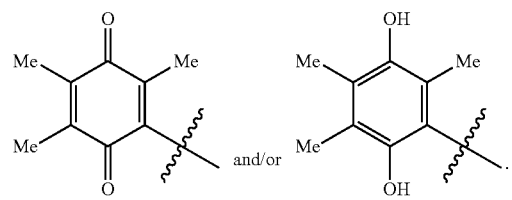 [SMILES: *C1=C(C)C(=O)C(C)=C(C)C1=O ; *c1c(C)c(O)c(C)c(C)c1O]

In some embodiments, X has a structure:

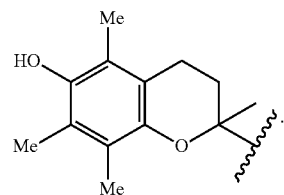 [SMILES: *C1(C)CCc2c(C)c(O)c(C)c(C)c2O1]

Thus, in some embodiments, the PBICs of the presently disclosed subject matter can have a structure as shown in Scheme 3, below, where n is an integer between 1 and 15 (e.g. 1, 2, 3, 4, 5, 6, 7, 8, 9, 10, 11, 12, 13, 14, or 15). In some embodiments, X is other than:

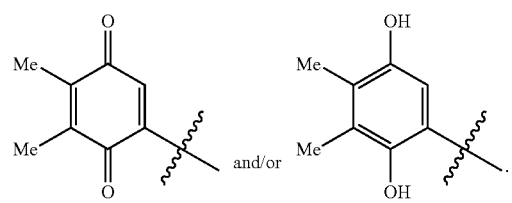 [SMILES: *C1=CC(=O)C(C)=C(C)C1=O ; *c1cc(O)c(C)c(C)c1O]

In some embodiments, the cationic compound is a cationic compound other than SkQ1.

Scheme 3. Exemplary PBICs.

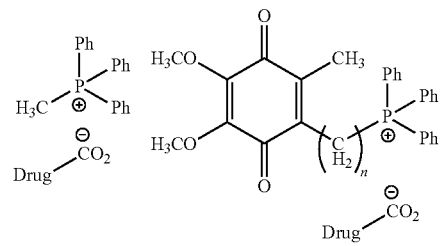

-continued

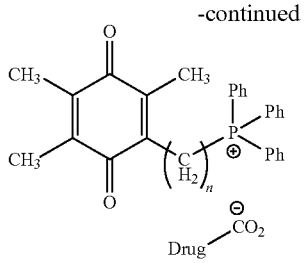

As noted above, the anionic compound component of the instantly disclosed compounds are pharmaceutically active compounds (including active metabolites of other pharmaceutically active compounds), or prodrugs or derivatives thereof. Thus, the anionic compound component of the conjugate is other than a halide or a mesylate group or another anionic group typically used as the anion of a salt form of a pharmaceutically active cationic compound.

More particularly, the pharmaceutically active compound, prodrug, or derivative thereof of the anionic component can be any suitable compound. In some embodiments, the pharmaceutically active compound is an active metabolite of another pharmaceutically active compound. In some embodiments, the pharmaceutically active compound is a compound for treating a disease, disorder, or condition selected from the group including, but not limited to, cancer; a disease, disorder, or condition associated with aging (e.g., dementia); a neurodegenerative disease, disorder or condition (such as, but not limited to, Alzheimer's disease, multiple sclerosis, or Parkinson's disease); sepsis; a hepatic disease, disorder or condition (such as, but not limited to, steatosis or cirrhosis); a kidney disease, disorder or condition; a cardiovascular disease, disorder, or condition (such as, but not limited to, hypertension, arrhythmia, angina, or stroke); diabetes or a related condition (such as, but not limited to, hyperglycemia, hypoglycemia, and diabetic neuropathy); Duchenne muscular dystrophy; a pulmonary disease, disorder, or condition (such as, but not limited to, an allergy, asthma, chronic obstructive pulmonary disease (COPD), cystic fibrosis, congestion, cough, or mucus); arthritis (such as, but not limited to osteoarthritis or rheumatoid arthritis); inflammation or an inflammatory disease or disorder; an immune system disease, disorder, or condition (e.g., an autoimmune disease, such as lupus or rheumatoid arthritis); an eye disease, disorder, or condition (such as, but not limited to, glaucoma, dry eye syndrome, age-related macular degeneration (AMD) or an eye infection); an infection, such as a bacterial, fungal, or viral infection (including, but not limited to, malaria and tuberculosis); pain; a central nervous system (CNS) disease, disorder or condition (such as, but not limited to, psychosis, schizophrenia, convulsions, anxiety, insomnia, autism, or attention deficit disorder (ADD)); a gastrointestinal disease, disorder or condition (such as, but not limited to, a digestion disorder, hyperacidity, nausea, diarrhea, or constipation); obesity; a sleep disorder; a metabolic disorder (such as, but not limited to, hyper- or hypo-thyroidism); a dermatologic disease, disorder, or condition (such as, but not limited to inflammatory like alopecia and keratinizing skin disorders (e.g., psoriasis and the like)); a wound, disease, disorder or condition relating to hair loss (e.g. such as alopecia or hair growth stimulation); a circulatory disease, disorder, or condition (such as, but not limited to, coronary, cerebral, or peripheral artery disease); osteoporosis; blood clotting; organ transplantation; fever; and a nutritional disease, disorder or condition, such as, but not limited to a vitamin, mineral or other nutritional deficiency or fat reduction.

Thus, the pharmaceutically active compound can be a compound or a prodrug or derivative of a pharmaceutically active compound (or an active metabolite of a pharmaceutically active compound), such as, but not limited to, fexofenadine, dabigatran, tirofiban, sulfasalazine, alitretinoin, azacitidine, bendamustine, bexarotene, bortezomib, chlorambucil, cladribine, clofarabine, cytarabine, decitabine, floxuridine, fludarabine, gemcitabine, isotretinoin, melphalan, mercaptopurine, methotrexate, panobinostat, pazopanib, pemetrexed, raltitrexed, tam ibarotene, tretinoin, vinblastine, vincristine, vinflunine, vinorelbine, vorinostat, atorvastatin, rosuvastatin, pravastatin, niacin, fluvastatin, fenofibrate, sumatriptan, baclofen, repaglinide, nateglinide, amphoterisin B, valproate, esmolol, eplerenone, clopidogrel acid, valsartan, trandolapril, telmisartan, ram ipril, quinapril, perindopril, nisoldipine, nimodipine, nicardipine, moexipril, lisinopril, isradipine, fosinopril, eprosartan, enalapril, cerivastatin, captopril, benazepril, amlodipine, qunilone antibacterials (such as, but not limited to, ofloxacin, ciprofloxacin, levofloxacin, temafloxacin, etc.), chloramphenicol, cefditoren, celecoxib, naproxen, ketorolac, ketoprofen, ibuprofen, fenoprofen, diclofenac, penicillamine, pregabalin, gabapentin, levodopa, carbidopa, clorazepic acid, selective thyroid hormone modulators (such as, but not limited to, levothyroxine, thyroxin, liothyronine, sobetirome, eprotirome, diiodothyropropionic acid, etc.), prostaglandins and prostacyclins (such as, but not limited to, unoprostone, treprostinil, beraprost, aloprostadil, travoprost, bimatoprost, latanoprost, tafluprost, iloprost, cicaprost, epiprostenol, etc.), setipiprant, timapiprant, elvitegravir, emtricitabine, tenofovir, oseltamivir, tenofovir, sofosbuvir, zidovudine, zalcitabine, ganciclovir, adefovir, robenacoxib, risedronic acid, tranexamic acid, tenofovir acid, minocycline, ursodeoxycholic acid, chenodeoxycholic acid, hyodeoxycholic acid, obeticholic acid, doxorubicin, methotrexate, histone deacylase inhibitors (such as, but not limited to, vorinostat, panabinostat, pracinostat, givinostat, belinostat, sodium butyrate, sodium phenylbutyrate, CUDC-101, JNJ-26481585, CRA-24781, and sodium valproate), prostacyclin receptor (IP receptor) antagonists (such as, but not limited to, 2-(3-(4,5-diphenyl-[2,4'-bioxazol]-5-yl)phenoxy)acetic acid, 3-(4-fluorophenyl)-2-(5-(4-fluorophenyl)benzofuran-2-yl)(methoxycarbonyl)amino) propanoic acid, (R)-3-phenyl-2-((((5-phenylbenzofuran-2-yl)methoxy) carbonyl)amino) propanoic acid and the like described, for example, in U.S. Pat. No. 9,321,745 B2, incorporated herein by reference in its entirety, and clinical candidates NS304, FK788, ONO1301 and APD811), selexipag active metabolites (e.g., ACT-333679 or MRE-269), curcumin, squalamine, pantothenic acid, biotin, and folic acid. Structures of particular exemplary anionic drugs that can be used as the pharmaceutically active compound of the presently disclosed PBICs are shown below in Scheme 4.

Scheme 4. Exemplary anionic drugs.

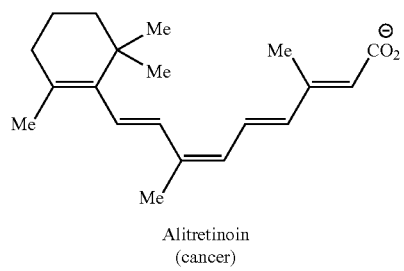

Alitretinoin
(cancer)

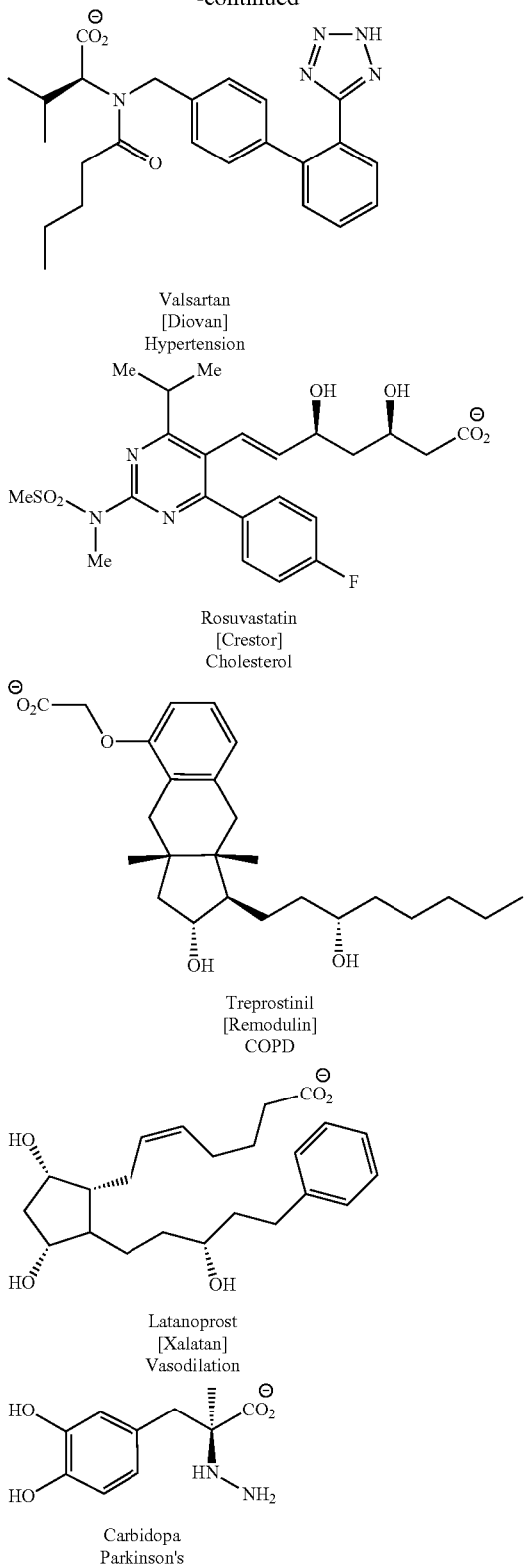

cancer agent; a non-steroidal anti-inflammatory drug (NSAID); a central nervous system (CNS) agent; a cholesterol lowering agent; a diabetes treatment agent; a hypertension treatment agent; a quinolone antibacterial; an osteoporosis drug; and a neuropathic pain agent. In some embodiments, the prostaglandin acid, prostacyclin acid or analog thereof is bimatoprost. In some embodiments, the statin is rosuvastatin. In some embodiments, the retinoid is alitretinoin. In some embodiments, the angiotensin receptor blocker is valsartan. In some embodiments, the vasodialator is treprostinil. In some embodiments, the dopa decarboxylase inhibitor is carbidopa. In some embodiments, the anticancer agent is methotrexate. In some embodiments, the NSAID is ibuprofen. In some embodiments, the CNS therapeutic agent is baclofen. In some embodiments, the cholesterol lowering agent is rosuvastatin. In some embodiments, the diabetes treatment agent is repaglinide. In some embodiments, the hypertension agent is valsartan. In some embodiments, the quinolone antibacterial is levofloxacin. In some embodiments, the osteoporosis drug is risedronic acid. In some embodiments, the neuropathic pain agent is pregabalin.

In some embodiments, the pharmaceutically active compound, prodrug, or derivative thereof comprises one or more (e.g., one or two) groups selected from an organic acid (e.g., a carboxylic acid, a sulfonic acid, a sulfenic acid, a boronic acid, a hydroxamic acid, a barbituric acid, an amino acid, a phosphonic acid, a phosphoric acid, etc.), an oxime, a hydroxyl, a phenol, a sulfonamide, a thiol, a uracil, a thiouracil, an amidine, a nitro ketone, a cyano ketone, a sulfone ketone, and a diketone. In some embodiments, the compound, prodrug, or derivative thereof comprises one or more anionic moieties derived from a carboxylic acid, a sulfonic acid, a phosphonic acid, a boronic acid, a hydroxamic acid, or a hydroxyl group. In some embodiments, the anionic moiety is derived from a carboxylic acid (i.e., is a carboxylate group of the formula —C(=O)O$^-$).

Thus, in some embodiments, the presently disclosed subject matter is directed to the phosphonium group-based ionic conjugates described above and to a method of improving the therapeutic index of a drug. The so conjugated drugs described herein have the same utility as that drug without the conjugation. Additionally, they have advantages not realized relative to the drug without the conjugation. For example, the presently disclosed subject matter can improve bioavailability and efficacy, reduce toxicity, improve solubility, enhance drug transport through the cell membranes or through the blood brain barrier, reduce side effects, and improve the therapeutic index and the like. The phosphonium group-based ionic conjugates in the presently disclosed subject matter have at least one improved quality and, preferably, have at least two or more of the improved qualities described herein. The phosphonium group-based ionic conjugates of the presently disclosed subject matter encompass pharmaceutically acceptable solvates, clathrates, enantiomers, diastereomers, polymorphs, co-crystals, or non-covalent derivatives and they can be associated along with pharmaceutically acceptable excipients and made into pharmaceutical or cosmetic compositions by techniques known to one skilled in the art.

IV. Pharmaceutical, Veterinary, and Cosmetic Formulations

In some embodiments, the pharmaceutical, veterinary, or cosmetic formulations comprising the PBICs are also are provided herein. These formulations can comprise PBICs as In some embodiments, the pharmaceutically active compound is selected from the group including, but not limited to a prostaglandin acid, prostacyclin acid, or an analog thereof; a statin; a retinoid; an angiotensin receptor blocker; a vasodialator; a dopa decarboxylase inhibitor; an antidescribed herein, in a pharmaceutically acceptable carrier. Pharmaceutical formulations can be prepared for oral, intravenous, subcutaneous, intramuscular, transdermal, topical, sublingual, subcutaneous, buccal, rectal, intraperitoneal, intrathecal, intravitreal, intraocular, aerosol, and nasal administration, as discussed in greater detail below. Also, the presently disclosed subject matter provides such PBICs that have been lyophilized and that can be reconstituted to form pharmaceutically acceptable formulations for administration, for example, as by intravenous or intramuscular injection.

The therapeutically effective dosage of any PBIC and/or particular pharmaceutically active compound component thereof, the use of which is within the scope of embodiments described herein, can vary from conjugate to conjugate, pharmaceutically active compound to pharmaceutically active compound, and/or patient to patient, and can depend upon the activity of the pharmaceutically active compound, the condition of the patient, and the route of delivery. For example, bimatoprost is typically administered at 2.5 micrograms per day, or approximately 0.025 micrograms per kg assuming a 100 kg patient. Similarly, Ciprofloxacin can be administered at 1000 mg per day, or 10 mg/kg for a 100 kg patient. As a general proposition, the dosage of the conjugates in this invention will not exceed the effective dose of the therapeutically active compound in it based on the improved absorption, transport, and bioavailability afforded by the conjugate. These dosage ranges are merely exemplary, and daily administration can be adjusted depending on various factors. The specific dosage of the phosphonium drug conjugate to be administered, as well as the duration of treatment, and whether the treatment is topical or systemic are interdependent. The dosage and treatment regimen can also depend upon such factors as the specific phosphonium drug conjugate used, the treatment indication, the efficacy of the compound, the personal attributes of the subject (such as, for example, weight, age, gender, and medical condition of the subject), compliance with the treatment regimen, and the presence and severity of any side effects of the treatment. The physician can determine the dosage of the conjugated drug of the presently disclosed subject matter which will be most suitable and which will vary based on form of administration and conjugated drug chosen. Generally, when the drug conjugate is administered orally, larger quantities of the drug conjugate of the present invention will be required to produce the same effect as a smaller quantity given parenterally. Toxicity concerns at the higher level can restrict intravenous dosages to a lower level. For example, a dosage from about 1 µg/kg/day to about 20 mg/kg/day can be employed for oral administration with all weights being calculated based on the weight of the active compound component. Typically, a dosage from about 0.02 µg/kg to 10 mg/kg can be employed for parenteral administration.

In a preferred embodiment, dosages are 0.02 µg/kg/day to 8 mg/kg/day, and more preferably 0.02 µg/kg/day and 5 mg/kg/day of the compound for intravenous or oral administration. The duration of the treatment is usually once per day for a period of two to three weeks or until the condition is essentially controlled. Lower doses given less frequently can be used prophylactically to prevent or reduce the incidence of recurrence of the disease, disorder, or condition or a symptom thereof.

The presently disclosed composition can be a pharmaceutical, veterinary, or cosmetic composition. Standard pharmaceutical formulation techniques are used, such as those disclosed in *Remington's Pharmaceutical Sciences*, Mack Publishing Company, Easton, Pa. (1990). The composition can comprise component (A) the phosphonium drug conjugate described above and component (B) a carrier. The composition can further comprise component (C) one or more optional activity enhancers.

As used herein, "carrier" can refer to one or more compatible substances (i.e., substances that are compatible (e.g., non-reactive) with the drug conjugate) and that are suitable for administration to a mammal. Carriers include solid or liquid diluents, hydrotopes, surface-active agents, and encapsulating substances. Carriers can be of sufficiently high purity and sufficiently low toxicity to render them suitable for administration to the subject (e.g., the mammal) being treated. The carrier can be inert, or it can possess pharmaceutical benefits, cosmetic benefits, or both.

The choice of carrier for component (B) depends on the route by which the phosphonium drug conjugate is to be administered and the form of the composition. The composition can be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis). In some embodiments, topical administration directly to the locus of desired effect is preferred. In some embodiments, systemic administration is preferred depending on the disease or condition.

Carriers for systemic administration typically comprise one or more ingredients selected from the group consisting of (a) diluents, (b) lubricants, (c) binders, (d) disintegrants, (e) colorants, (f) flavors, (g) sweeteners, (h) antioxidants, (i) preservatives, (j) glidants, (k) solvents, (l) suspending agents, (m) surfactants, combinations thereof, and others.

Ingredient (a) is a diluent. Suitable diluents include, but are not limited to, sugars such as glucose, lactose, dextrose, and sucrose; polyols such as propylene glycol; calcium carbonate; sodium carbonate; glycerin; mannitol; sorbitol; and maltodextrin.

Ingredient (b) is a lubricant. Suitable lubricants are exemplified by solid lubricants, including silica, talc, stearic acid and its magnesium salts and calcium salts, and calcium sulfate; and liquid lubricants, such as polyethylene glycol and vegetable oils such as peanut oil, cottonseed oil, sesame oil, olive oil, corn oil, and oil of theobroma.

Ingredient (c) is a binder. Suitable binders include, but are not limited to, polyvinylpyrrolidone; magnesium aluminum silicate; starches, such as corn starch and potato starch; gelatin; tragacanth; and cellulose and its derivatives, such as sodium carboxymethylcellulose, ethylcellulose, methylcellulose, microcrystalline cellulose, and hydroxypropylmethylcellulose; carbomer; providone; acacia; guar gum; and xanthan gum.

Ingredient (d) is a disintegrant. Suitable disintegrants include, but are not limited to, agar, alginic acid and the sodium salt thereof, effervescent mixtures, croscarmelose, crospovidone, sodium carboxymethyl starch, sodium starch glycolate, clays, and ion exchange resins.

Ingredient (e) is a colorant, such as, but not limited to an FD&C dye.

Ingredient (f) is a flavor such as, but not limited to, menthol, peppermint, and fruit flavors.

Ingredient (g) is a sweetener, such as, but not limited to, saccharin and aspartame.

Ingredient (h) is an antioxidant such as, but not limited to, butylated hydroxyanisole, butylated hydroxytoluene, and vitamin E.

Ingredient (i) is a preservative such as, but not limited to, phenol, alkyl esters of parahydroxybenzoic acid, benzoic acid and the salts thereof, boric acid and the salts thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben, and sodium benzoate.

Ingredient (j) is a glidant such as, but not limited to, silicon dioxide.

Ingredient (k) is a solvent, such as, but not limited to, water, isotonic saline, ethyl oleate, alcohols such as ethanol, glycerin, glycols (e.g., polypropylene glycol and polyethylene glycol), and buffer solutions (e.g., phosphate, potassium acetate, boric carbonic, phosphoric, succinic, malic, tartaric, citric, acetic, benzoic, lactic, glyceric, gluconic, glutaric and glutamic).

Ingredient (l) is a suspending agent. Suitable suspending agents include, for example, AVICEL® (FMC Corp., Philadelphia, Pa., United States of America), and sodium alginate.

Ingredient (m) is a surfactant such as, but not limited to, lecithin, polysorbate 80, sodium lauryl sulfate, polyoxyethylene sorbitan fatty acid esters, polyoxyethylene monoalkyl ethers, sucrose monoesters, lanolin esters, and lanolin ethers. Suitable surfactants are known in the art and commercially available, e.g., the TWEENS® (Croda International, PLC; Snaith, United Kingdom).

Compositions for parenteral administration typically comprise: (A) 0.01 to 10% of a phosphonium drug conjugate and (B) 90 to 99.99% of a carrier comprising (a) a diluent, and (k) a solvent. Preferably, component (a) is propylene glycol and (k) is water, ethanol, and/or ethyl oleate.

Compositions for oral administration can have various dosage forms. For example, solid forms include tablets, capsules, granules, and bulk powders. These oral dosage forms can comprise a safe and effective amount, usually at least 5%, and preferably from 25% to 50%, of (A) the phosphonium drug conjugate. The oral dosage compositions can further comprise component (B), i.e., 50 to 95% of a carrier, preferably 50 to 75% of a carrier.

Tablets can be compressed, tablet triturates, enteric-coated, sugar-coated, film-coated, or multiple-compressed. Tablets typically comprise (A) the phosphonium drug conjugate, and (B) a carrier comprising ingredients selected from the group comprising: (a) diluents, (b) lubricants, (c) binders, (d) disintegrants, (e) colorants, (f) flavors, (g) sweeteners, (j) glidants, and combinations thereof. Preferred diluents include, but are not limited to, calcium carbonate, sodium carbonate, mannitol, lactose and cellulose. Preferred binders include, but are not limited to, starch, gelatin, and sucrose. Preferred disintegrants include, but are not limited to, alginic acid, and croscarmelose.

Preferred lubricants include, but are not limited to, magnesium stearate, stearic acid, and talc. Preferred colorants include, for example, the FD&C dyes, which can be added for appearance. Chewable tablets preferably contain (g) sweeteners, such as aspartame and saccharin, and/or (f) flavors, such as menthol, peppermint, and fruit flavors.

Capsules (including time release and sustained release formulations) typically comprise (A) the phosphonium drug conjugate, and (B) a carrier comprising one or more (a) diluents disclosed above in a capsule comprising gelatin.

Granules typically comprise (A) the phosphonium drug conjugate, and preferably further comprise (j) glidants, such as, but not limited to, silicon dioxide to improve flow characteristics.

The selection of ingredients in the carrier for oral compositions can depend on secondary considerations, like taste, cost, and shelf stability, which are not critical for the purposes of the presently disclosed subject matter. One skilled in the art can optimize appropriate ingredients without undue experimentation.

The solid compositions can also be coated by conventional methods, typically with pH or time-dependent coatings, such that (A) the phosphonium drug conjugate is released in the gastrointestinal tract at various times to extend the desired action. The coatings typically comprise one or more components selected from the group comprising, for example, cellulose acetate phthalate, polyvinylacetate phthalate, hydroxypropyl methyl cellulose phthalate, ethyl cellulose, acrylic resins such as EUDRAGIT® (Evonik Industries, Essen, Germany) coatings, waxes, shellac, polyvinylpyrrolidone, and other commercially available film-coating preparations such as Dri-Klear, or OPADRY® (COLORCON®, Harleysville, Pa., United States of America).

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise (A) the phosphonium drug conjugate and (B) a carrier comprising ingredients selected from the group comprising: (a) diluents, (e) colorants, and (f) flavors, (g) sweeteners, (i) preservatives, (k) solvents, (I) suspending agents, and (m) surfactants. Peroral liquid compositions preferably comprise one or more ingredients selected from the group comprising (e) colorants, (f) flavors, and (g) sweeteners.

Other compositions useful for attaining systemic delivery of the subject conjugates include sublingual, buccal and nasal dosage forms. Such compositions typically comprise one or more of soluble filler substances, such as, but not limited to, (a) diluents, including sucrose, sorbitol and mannitol; and (c) binders, such as acacia, microcrystalline cellulose, carboxymethylcellulose, and hydroxypropylmethyl cellulose. Such compositions can further comprise lubricants, colorants, flavors, sweeteners, antioxidants, and glidants.

The compositions can further comprise component (C), an optional activity enhancer. In some embodiments, the optionally activity enhancer is selected such that it is specific to the drug conjugate. For example, for a hair growth composition comprising bimatoprost acid drug conjugate, component (C) can be selected from the group comprising (i) hair growth stimulants (other than the phosphonium drug conjugate), such as, but not limited to, vasodilators, antiandrogens, cyclosporins, cyclosporin analogs, antimicrobials, anti-inflammatories, thyroid honnones, thyroid hormone derivatives, thyroid hormone analogs, non-selective prostaglandin agonists or antagonists, retinoids, triterpenes, and combinations thereof, and the like; and (ii) penetration enhancers, such as, but not limited to, 2-methyl propan-2-ol, propan-2-ol, ethyl-2-hydroxypropanoate, hexan-2,5-diol, polyoxyethylene(2) ethyl ether, di(2-hydroxypropyl) ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, omega three fatty acids and fish oils, and combinations thereof.

Pharmaceutical formulations also are provided which are suitable for topical administration. Topical compositions that can be applied locally to the skin can be in any form, including solutions, oils, creams, ointments, gels, lotions, shampoos, leave-on and rinse-out hair conditioners, milks, cleansers, moisturizers, sprays, skin patches, and the like. Topical compositions can comprise: component (A) the phosphonium drug conjugate described above and component (B) a carrier. The carrier of the topical composition preferably aids penetration of the phosphonium drug conjugates into the skin.

The exact amounts of each component in the topical composition can depend on various factors. The amount of component (A) can depend on the $IC_{50}$ of the phosphonium drug conjugate selected. "$IC_{50}$" means inhibitory concentration 50th percentile. In some embodiments, the amount of component (A) added to the topical composition is:

$$IC_{50} \times 10^{-2} \geq \% \text{ of component } (A) \geq IC_{50} \times 10^{-3}$$

where $IC_{50}$ is expressed in nanomolar units. For example, if the $IC_{50}$ of the phosphonium drug conjugate is 1 nM, the amount of component (A) can be 0.001 to 0.01%. If the $IC_{50}$ of the phosphonium drug conjugate is 10 nM, the amount of component (A) can be 0.01 to 0.1%. If the $IC_{50}$ of the phosphonium drug conjugate is 100 nM, the amount of component (A) can be 0.1 to 1.0%. If the $IC_{50}$ of the phosphonium drug conjugate is 1000 nM, the amount of component (A) can be 1.0 to 10%, preferably 1.0 to 5%. If the amount of component (A) is outside the ranges specified above (i.e., either higher or lower), efficacy of the treatment can be reduced. One skilled in the art can calculate $IC_{50}$ without undue experimentation. Techniques and compositions for making dosage forms useful in the methods of the presently disclosed subject matter are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* 2nd Ed., (1976).

Component (B) the carrier can comprise a single ingredient or a combination of two or more ingredients. In the topical compositions, Component (B) is a topical carrier. Preferred topical carriers can comprise one or more ingredients selected from the group comprising water, alcohols, aloe vera gel, allantoin, glycerin, vitamin A and E oils, mineral oil, propylene glycol, polypropylene glycol-2 myristyl propionate, dimethyl isosorbide, combinations thereof, and the like. More preferred carriers include propylene glycol, dimethyl isosorbide, and water.

The topical carrier can comprise one or more ingredients selected from the group comprising (q) emollients, (r) propellants, (s) solvents, (t) humectants, (u) thickeners, (v) powders, and (w) fragrances, in addition to, or instead of, the preferred topical carrier ingredients listed above. One skilled in the art would be able to optimize carrier ingredients for the topical compositions without undue experimentation.

Ingredient (q) is an emollient. The amount of ingredient (q) in the topical composition is typically 5 to 95%. Suitable emollients include, but are not limited to, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, polydimethylsiloxane, and combinations thereof. Preferred emollients include stearyl alcohol and polydimethylsiloxane.

Ingredient (r) is a propellant. The amount of ingredient (r) in the topical composition is typically 5 to 95%. Suitable propellants include, but are not limited to, propane, butane, isobutane, dimethyl ether, carbon dioxide, nitrous oxide, and combinations thereof.

Ingredient (s) is a solvent. The amount of ingredient (s) in the topical composition is typically 5 to 95%. Suitable solvents include, but are not limited to, water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient (t) is a humectant. The amount of ingredient (t) in the topical composition is typically 5 to 95%. Suitable humectants include, but are not limited to, glycerin, sorbitol, sodium 2-pyrrolidone-5-carboxylate, soluble collagen, dibutyl phthalate, gelatin, and combinations thereof. Preferred humectants include glycerin.

Ingredient (u) is a thickener. The amount of ingredient (u) in the topical composition is typically 0 to 95%.

Ingredient (v) is a powder. The amount of ingredient (v) in the topical composition is typically 0 to 95%. Suitable powders include, but are not limited to, chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient (w) is a fragrance. The amount of ingredient (w) in the topical composition is typically 0.001 to 0.5%, preferably 0.001 to 0.1%.

Component (C), the optional activity enhancer, is as described above.

In an alternative embodiment of the presently disclosed subject matter, topical pharmaceutical compositions for ocular administration are prepared by conventional methods. Topical pharmaceutical compositions for ocular administration typically comprise (A) a phosphonium drug conjugate, (B) a carrier, such as purified water, and one or more ingredients selected from the group comprising (y) sugars, such as dextrans, particularly dextran 70, (z) cellulose or a derivative thereof, (aa) a salt, (bb) disodium EDTA (Edetate disodium), and (cc) a pH adjusting additive.

Examples of (z) cellulose derivatives suitable for use in the topical pharmaceutical composition for ocular administration include, but are not limited to, sodium carboxymethyl cellulose, ethyl cellulose, methyl cellulose, and hydroxypropylmethylcellulose. Hydroxypropylmethylcellulose is preferred.

Examples of (aa) salts suitable for use in the topical pharmaceutical composition for ocular administration include, but are not limited to, sodium chloride, potassium chloride, and combinations thereof.

Examples of (cc) pH adjusting additives include, but are not limited to, HCl or NaOH in amounts sufficient to adjust the pH of the topical pharmaceutical composition for ocular administration to 7.2-7.5.

In some embodiments, the topical composition can be, for example, a cosmetic composition prepared as described above. An example of a cosmetic composition that can be applied to eyelashes is a mascara. The phosphonium drug conjugate can be added to mascara compositions known in the art, such as the mascara described in U.S. Pat. No. 5,874,072, which is hereby incorporated by reference in its entirety. The mascara can further comprise (dd) a water-insoluble material, (ee) a water-soluble film-forming polymer, (ff) a wax, (m) a surfactant, gg) a pigment, and (k) a solvent.

Ingredient (dd) is a water-insoluble material selected from the group comprising acrylate copolymers; styrene/acrylate/methacrylate copolymers; acrylic latex; styrene/acrylic ester copolymer latex; polyvinylacetate latex; vinyl acetate/ethylene copolymer latex; styrene/butadiene copolymer latex; polyurethane latex; butadiene/acrylonitrile copolymer latex; styrene/acrylate/acrylonitrile copolymer latex; and mixtures thereof, wherein the acrylate copolymers, and the styrene/acrylate/methacrylate copolymers additionally comprise ammonia, propylene glycol, a preservative and a surfactant.

Ingredient (ee) is a water-soluble, film-forming polymer. Ingredient (ee) is selected from the group comprising vinyl alcohol/poly(alkyleneoxy)acrylate, vinyl alcohol/vinyl acetate/poly-(alkyleneoxy)acrylate, polyethylene oxide, polypropylene oxide, acrylates/octyl-acrylamide copolymers and mixtures thereof.

Ingredient (ff) is a wax. "Wax" means a lower-melting organic mixture or compound of high molecular weight, solid at room temperature and generally similar in composition to fats and oils except that they contain no glycerides. Some are hydrocarbons, others are esters of fatty acids and alcohols. Waxes useful in the presently disclosed subject matter are selected from the group comprising animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55 and 100° C.

Ingredient (m) is surfactant, as described above. Ingredient (m) in the mascara is preferably a surfactant having an HLB from 3 to 15. Suitable surfactants include those disclosed in the C.T.F.A. Cosmetic Ingredient Handbook, pp. 587-592 (1992); Remington's Pharmaceutical Sciences, 15th ed., pp. 335-337 (1975); and McCutcheon's Volume 1, Emulsifiers & Detergents, North American Edition, pp. 236-239 (1994).

Ingredient (gg) is a pigment. Suitable pigments include, but are not limited to, inorganic pigments, organic lake pigments, pearlescent pigments, and mixtures thereof. Inorganic pigments useful in the presently disclosed subject matter include those selected from the group comprising rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510); and mixtures thereof.

The organic pigments and lakes useful in the presently disclosed subject matter include those selected from the group comprising D&C Red No. 19 (CI 45,170), D&C Red No. 9 (CI 15,585), D&C Red No. 21 (CI 45,380), D&C Orange No. 4 (CI 15,510), D&C Orange No. 5 (CI 45:370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), and the dye or lakes based on Cochineal Carmine (CI 75,570), and mixtures thereof.

The pearlescent pigments useful in the presently disclosed subject matter include those selected from the group comprising the white pearlescent pigments, such as mica coated with titanium oxide; bismuth oxychloride; colored pearlescent pigments, such as titanium mica with iron oxides; titanium mica with ferric blue, chromium oxide and the like; titanium mica with an organic pigment of the above-mentioned type, as well as those based on bismuth oxychloride and mixtures thereof.

Ingredient (k) is a solvent described above, preferably water.

The amount of (A) the phosphonium drug conjugate added to the mascara is as described above for topical compositions.

In accordance with the present methods, PBICs as described herein can be administered orally as a solid or as a liquid, or can be administered intramuscularly or intravenously as a solution, suspension, or emulsion. Alternatively, the PBICs also can be administered by inhalation, intravenously, or intramuscularly as a liposomal suspension. When administered through inhalation the PBIC can be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a PBIC as described herein in any pharmaceutically acceptable carrier. If a solution is desired, water is the carrier of choice with respect to water-soluble compounds or salts. With respect to the water-soluble PBICs, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to the PBIC, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a PBIC, in a unit dosage form in a sealed container. The PBIC is provided in the form of a lyophilizate, which is capable of being reconstituted with a suitable pharmaceutically acceptable carrier to form a liquid formulation suitable for injection thereof into a subject. The unit dosage form typically comprises from about 0.01 μg to about 1 g of the PBIC, or between about 0.01 μg to about 25 mg of the PBIC.

Other pharmaceutical formulations can be prepared as emulsions. In such an instance, the formulation will contain a sufficient amount of pharmaceutically acceptable emulsifying agent to emulsify the desired amount of the PBIC. Particularly useful emulsifying agents include phosphatidyl cholines and lecithin.

Additional embodiments provided herein include liposomal formulations (small unilamellar vesicles, large unilamellar vesicles, and multilamellar vesicles) of the PBICs disclosed herein. The technology for forming liposomal suspensions is well known in the art. When the PBIC is an aqueous-soluble salt, using conventional liposome technology, the same can be incorporated into lipid vesicles. In such an instance, due to the water solubility of the PBIC, the PBIC will be substantially entrained within the hydrophilic center or core of the liposomes. The lipid layer employed can be of any conventional composition and can either contain cholesterol or can be cholesterol-free. When the PBIC of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

Liposomes can be formed from a variety of phospholipids, such as cholesterol, stearylamine or phosphatidylcholines. A preferred formulation for topical delivery of the present compounds uses liposomes as described in Dowton et al., S.T.P. Pharma Sciences 1993, 3: 404-407; Wallach and Philippot, Liposome Technology 1993, 1: 141-156; U.S. Pat. Nos. 4,911,928; and 5,834,014 (with respect to U.S. Pat. No. 5,834,014, with a compound as described herein administered in lieu of, or in addition to, minoxidil).

The liposomal formulations comprising the PBICs disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration by iontophoresis. See, e.g. Banga et al., Pharm. Res. 1993, 10 (5): 697-702; Ferry, Pharmaceutical Acta Helvetiae 1995, 70: 279-287; Gangarosa et al., Int. J. Pharm. 1995, 123: 159-171; Green et al., Pharm. Res. 1991, 8: 1121-1127; Jadoul et al., Int. J. Pharm. 1995, 120: 221-8; O'Brien et al., Drugs 1989, 37: 233-309; Parry et al., J. Invest. Dermatol. 1992, 98(6): 856-63; Santi et al., Pharm. Res. 1997, 14(1): 63-66; Santi et al., J. Control. Release 1996, 38: 159-165; Santi et al., J. Control. Release 1996, 42: 29-36; Rao et al., Pharm. Res. 1995, 12(12): 1869-1873; Thysman et al., J. Pharm. Pharmacol. 1994, 46: 725-730; and Volpato et al., Pharm. Res. 1995, 12(11): 1623-1627.

Pharmaceutical formulations also are provided which are suitable for administration as an aerosol by inhalation. These formulations can comprise a solution or suspension of a desired PBIC as described herein, or a plurality of solid particles of the PBIC. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid PBIC thereof, in any appropriate manner known in the art, such as by micronization. Most preferably, the size of the solid particles or droplets will be from about 1 to about 2 microns. In this respect, commercial nebulizers are available to achieve this purpose. The PBICs can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble PBIC in a carrier that comprises water. A surfactant can be present, which lowers the surface tension of the formulation sufficiently to result in the formation of droplets within the desired size range when subjected to nebulization.

As indicated, both water-soluble and water-insoluble PBICs are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/m L. In some embodiments, water-soluble compounds or salts can be desirable whereas in other embodiments water-insoluble compounds or salts likewise can be desirable.

Increased ionic strength of formulations comprising ion paired drugs can, in some embodiments, provide increased 1-octanol/buffer distribution coefficients. Thus, in some embodiments, the ionic strength of the pharmaceutical formulation of the PBIC of the presently disclosed subject matter can varied to adjust the distribution coefficient. For example, in some embodiments, the pharmaceutical formulation of the PBIC of the presently disclosed subject matter can be prepared to contain an excess of one of (a) the cationic compound comprising the phosphonium group or (b) the anionic compound comprising the pharmaceutically active compound or prodrug or derivative thereof. For instance, in some embodiments, rather than a 1:1 mixture of the cationic compound and the anionic compound of the PBIC, the formulation of the PBIC can include an up to 10 molar excess (e.g., a 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, or 10.0 molar excess) of either the cationic compound or the anionic compound. Alternatively, in some embodiments, the ionic strength of the PBIC formulation can be increased by the inclusion of an amount of an inorganic salt, such as, but not limited to, NaCl, KCl, LiCl, magnesium chloride, sodium phosphate, and sodium sulfate.

V. Methods of Treatment

In some embodiments, the presently disclosed subject matter provides a method of treating a disease, disorder or condition in a subject in need of treatment thereof, wherein the method comprises administering a PBIC as described herein or a pharmaceutical, veterinary, or cosmetic formulation thereof. The methods of the presently disclosed subject matter are useful for treating the diseases, disorders, or conditions in that they inhibit the onset, growth, or spread of the disease, disorder, or condition, cause regression of the disease, disorder or condition, cure the disease, disorder or condition, or otherwise improve the general well-being of a subject afflicted with, or at risk of, contracting the disease, disorder, or condition. Thus, in accordance with the presently disclosed subject matter, the terms "treat," "treating," and grammatical variations thereof, as well as the phrase "method of treating," are meant to encompass any desired therapeutic intervention, including but not limited to a method for treating an existing disease, disorder or condition in a subject, and a method for the prophylaxis (i.e., preventing) of a disease, disorder or condition, such as in a subject that has been exposed to an infectious agent or that has an expectation of being exposed to an infectious agent or who has a genetic predisposition and/or family history of a particular disease disorder or condition.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment and/or prevention of diseases, disorders or conditions in warm-blooded vertebrates. Thus, the methods can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), rodents (such as mice, rats, and hamsters), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos or as pets (e.g., parrots), as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

In some embodiments, the disease, disorder or condition being treated with the PBIC is selected from the group including, but not limited to, cancer; a disease, disorder, or condition associated with aging (e.g., dementia); a neurodegenerative disease, disorder or condition, such as, but not limited to, Alzheimer's disease, multiple sclerosis, or Parkinson's disease; sepsis; a kidney disease, disorder or condition; a hepatic disease, disorder or condition, such as, but not limited to, steatosis or cirrhosis; a cardiovascular disease, disorder, or condition, such as, but not limited to, hypertension, arrhythmia, angina, or stroke; diabetes or a related condition, such as, but not limited to, hyperglycemia, hypoglycemia or diabetic neuropathy; Duchenne muscular dystrophy; a pulmonary disease, disorder, or condition, such as, but not limited to, an allergy, asthma, chronic obstructive pulmonary disease (COPD), cystic fibrosis, congestion, cough, or mucus; arthritis, such as, but not limited to osteoarthritis or rheumatoid arthritis; inflammation or an inflammatory disease or disorder; an immune system disease, disorder, or condition; an eye disease, disorder, or condition, such as, but not limited to glaucoma, dry eye syndrome, age-related macular degeneration (AMD) or an eye infection; an infection, such as, but not limited to, a bacterial, fungal, or viral infection, including, for example, malaria or tuberculosis; pain; a central nervous system disease, disorder or condition, such as, but not limited to, psychosis, schizophrenia, convulsions, anxiety, insomnia, autism, or attention deficit disorder (ADD); a gastrointestinal disease, disorder or condition, such as, but not limited to, a digestion disorder, hyperacidity, nausea, diarrhea, or constipation; obesity; a sleep disorder; a metabolic disorder, such as, but not limited to, hyper- or hypo-thyroidism; a dermatologic disease, disorder, or condition, such as, but not limited to, inflammatory skin disorders like alopecia and keratinizing skin disorders like psoriasis, a wound, disease, disorder or condition relating to hair loss (e.g., alopecia or hair growth stimulation), a circulatory disease, disorder, or condition, such as, but not limited to, coronary, cerebral, or peripheral artery disease; osteoporosis; blood clotting; organ transplantation; fever; and a nutritional disease, disorder or condition, such as, but not limited to, a vitamin, mineral or other nutritional deficiency, and fat reduction.

The PBIC or pharmaceutical, veterinary or cosmetic formation thereof can be administered to the subject via any suitable route. In some embodiments, the route is selected from the group including, but not limited to oral, intravenous, subcutaneous, intramuscular, transdermal, topical, sublingual, subcutaneous, buccal, rectal, intraperitoneal, intrathecal, intravitreal, intraocular, aerosol, and nasal administration.

VI. Methods of Enhancing Pharmaceutical and/or Pharmacological Properties

In some embodiments, the presently disclosed subject matter provides a method of enhancing the pharmaceutical and/or pharmacological properties of a pharmaceutically active agent or prodrug thereof. In some embodiments, the method comprises: (a) providing a pharmaceutically active agent, or a prodrug or derivative thereof, wherein said pharmaceutically active agent, prodrug, or derivative comprises one or more anionic groups or moieties capable of forming an anionic group; and (b) contacting the pharmaceutically active agent, prodrug, or derivative with a compound comprising a phosphonium group under conditions suitable to form an ionic conjugate.

In some embodiments, enhancing the physicochemical, pharmacokinetic, pharmaceutical and/or pharmacological properties comprises increasing water solubility, hydrophilicity/hydrophobicity, permeability, absorption and/or bioavailability, increasing efficacy, reducing toxicity and/or side effects, improving cell membrane penetration, and/or improving blood brain barrier penetration compared to the pharmaceutical and/or pharmacological properties of the pharmaceutically active agent (i.e., when it is not part of a PBIC).

The compound comprising the phosphonium group can be any suitable phosphonium containing compound. In some embodiments, the compound comprising a phosphonium group has a structure of the formula:

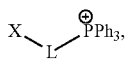

wherein L is an alkylene group and X is H or a monovalent residue of a compound comprising antioxidant properties. In some embodiments, L is a saturated or unsaturated, substituted or unsubstituted $C_1$-$C_{15}$ alkylene group. In some embodiments, X is a monovalent residue of a compound comprising antioxidant properties and the pharmaceutical compound prodrug or derivative thereof is a compound for use in treating a disease or disorder associated with oxidative stress. In some embodiments, the compound comprising the phosphonium group is other than SkQ1. In some embodiments, X is H. In some embodiments, the compound comprising the phosphonium group is TPMP or MitoQ.

In some embodiments, the suitable conditions comprise dissolving anionic form of the pharmaceutically active compound, prodrug or derivative thereof in a suitable solvent to prepare a first solution, dissolving the compound comprising the phosphonium group in a suitable solvent to prepare a second solution, and mixing the first and second solutions together. In some embodimetns, the solvent of the first and second solutions is the same. In some embodiments, the solvent or solvents is/are aprotic solvents, e.g., an ether, such as THF, a nitrile, or an ester (e.g., ethyl acetate). In some embodiments, the solvent or solvents are or include protic solvents (e.g., water, ethanol or methanol). In some embodiments, the solvent or solvents are removed after mixing. In some embodiments, a salt (e.g., an ammonium or alkali metal salt) of the anionic form of the pharmaceutically active compound, prodrug or derivative thereof is contacted with the compound comprising the phosphonium group or the corresponding phosphonium halide, mesylate, tosylate, or alkyl or aryl carbonate. In some embodiments, the pharmaceutically active compound, prodrug, deriviatve, and/or salt thereof is contacted with the methyl carbonate of the compound comprising the phosphonium group.

In some embodiments, the pharmaceutically acceptable compound, prodrug, or derivative thereof comprises a group of suitable pKa value such as a groups selected from the group comprising organic acids (e.g., carboxylic acid, sulfonic acid, sulfenic acid, boronic acid, hydroxamic acid, barbituric acid, aminoacid, phosphoric acid, phosphonic acid, etc.), oximes, hydroxyls, phenols, hydroxyl, sulfonamides, thiols, uracils, thiouracils, amidines, and certain ketones (nitro, cyano, sulfone, cyclic diketones).

In some embodiments, the pharmaceutically acceptable compound, prodrug, or derivative thereof comprises one or more carboxylic acid group (e.g., is a mono- or dicarboxylic acid). In some embodiments, the carboxylic acid is provided as an ammonium or alkali metal salt. In some embodiments, the carboxylic acid or ammonium or alkali metal salt thereof is provided in a suitable solvent, e.g., such as an alcohol (e.g., methanol or ethanol), a nitrile (e.g., acetonitrile), an ether (e.g., diethyl ether or THF), or an ester (e.g., ethyl acetate). The carboxylic acid or ammonium or alkali metal salt thereof can then be contacted with compound comprising a phosphonium halide (e.g., a phosphonium bromide) or a methyl carbonate of a phosphonium group. In some embodiments, the carboxylic acid or salt thereof is provided in a molar excess compared to the compound comprising the phosphonium halide or phosphonium methyl carbonate.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

The conjugates of the presently disclosed subject matter can be prepared by art recognized techniques. For example, the therapeutically active compounds in this invention have one or more acidic protons that can be converted to a suitable salt (e.g. alkali metal salt, ammonium salt, and the like) via deprotonation with a suitable base. They are brought in contact with an alkyl-triphenylphosphonium reagent (e.g. phosphonium halide, mesylate, tosylate, and the like) to form the phosphonium group-based ionic conjugate and the analogous alkali or ammonium salt, which is removed. The reaction can be carried in a suitable solvent. Suitable solvents include, but are not limited to, water, nitriles (e.g. acetonitrilepropionitrile, butyronitrile, valeronitrile, and the like), ethers (e.g. diethyl, dipropyl, dibutyl, diamyl ether, and the like), acetates (e.g. ethyl acetate, methyl acetate, isopropyl acetate, and the like), ketones (e.g. acetone, methyl isobutyl ketone, and the like), tetrahydrofuran, dioxane, dichloromethane, chloroform, or alcohols (e.g. methyl, ethyl, propyl, isopropyl, butyl, and the like). Preferred solvents for the reaction are those that solubilize both reactants such as water, alcohols, or other solvents in combination with these two. The products are isolated by methods known to one of ordinary skill in the art. Such methods include extraction, solvent evaporation, distillation, and crystallization. Preferred solvents for the isolation are those that do not solubilize the by-product sodium bromide or any unreacted phosphonium reagent such as diethyl ether, tetrahydrofuran, toluene, acetonitrile, acetone, and the like. The stoichiometry used for the reaction is typically one molequivalents of the drug salt to one molequivalents of phosphonium reagent. Preferably, a slight excess of the drug salt is used to ensure complete reaction. The reaction is monitored by HPLC or TLC to ensure completion. Preferably, the products are purified by techniques known to one skilled in the art, such as chromatography using a suitable support, crystallization, and the like.

Alternatively, the conjugates can be prepared by the pharmaceutically active compound, prodrug or derivative with a phosphonium alkyl or aryl carbonate (such as triphenylmethylphosphonium methyl carbonate) in a suitable solvent. See Caretto et al., Sciences at CA' Foscari 2012, 60-70.

The Examples below relate to PBICs of a variety of different therapeutic compounds. While initial attempts to prepare PBICs comprising SkQ1 as the cationic compound were unsuccessful, it is believed that this was the result of stability issues related to the SkQ1 compound itself under the particular conditions used, combined with the small scale of the reactions, rather than any inability of the SkQ1 compound to form an ionic conjugate. Without being bound to any one theory, it is believed that reduced temperature, inert atmosphere, and protection from light can be used to improve the stability of the SkQ1.

Example 1

Preparation of Ibuprofen Conjugates

Ibuprofen-TPMP Conjugate:

Method A: Ibuprofen sodium salt (1.0 moleq) and triphenylmethylphosphonium bromide (1.0 moleq) are added to methanol with stirring. The ion exchange is allowed to proceed until completion at 25-50° C. The reaction is monitored by TLC. Upon completion, acetonitrile is added to the reaction solution and the methanol is removed by distillation. The sodium bromide and any unreacted triphenylmethyl phosphonium bromide are removed by filtration. The remaining solution is further concentrated to afford the ibuprofen-TPMP conjugate, which typically is sufficiently pure at this stage. Further purification is attained by column chromatography on silca gel using dichloromethane and ethanol as eluents.

Method B: Ibuprofen (5 g; 24.3 mmol) and Triphenylmethylphosphonium methyl carbonate (8.1 g; 23 mmol) were stirred in 20 ml of ethanol at ambient temperature overnight. The reaction mixture was concentrated under vacuum at 60° C. to afford 11.2 g of Ibuprofen TPMP conjugate.

Ibuprofen-MitoQ Conjugate:

MitoQ mesylate (5 g; 7.4 mmol) and Ibuprofen sodium salt (2 g; 7.2 mmol) were added to flask containing 20 ml of brine, 50 ml of ethyl acetate and 4 ml of water. The reaction was stirred under inert atmosphere and protected from light for approximately 30 minutes. Dichloromethane (20 ml) was added to the reaction mixture and the two layers were separated. The organic layer was washed three times with a mixture of 20 ml of brine and 4 ml of water and one time with 20 ml of brine. The organic layer was then dried over sodium sulfate, filtered, and dried under high vacuum in the dark to afford 5 g of the Ibuprofen MitoQ conjugate.

Example 2

Preparation of Sulfasalazine-TPMP Conjugate

Method A: Sulfasalazine sodium salt (1.0 moleq) and triphenylmethylphosphonium bromide (1.0 moleq) are added to ethanol with stirring. The salt exchange is continued until completion at 25-50° C. The reaction is monitored by TLC. Upon completion, the ethanol is removed under vacuum. The crude sulfasalazine-TPMP conjugate is further purified by column chromatography on silca gel using chloroform and ethanol as eluents.

Method B: Sulfasalazine (7 g; 17.6 mmol) was suspended in 70 ml of ethanol and Triphenylmethylphosphonium methyl carbonate (5.88 g; 16.7 mmol) was added to it. The mixture was heated with stirring to 80° C. The reaction was stirred at 80° C. for one hour. It was then concentrated under vacuum at 50° C. The product was dried under high vacuum at 45° C. to afford 11.2 g of Sulfasalazine TPMP conjugate.

Example 3

Preparation of Elvitegravir-TPMP Conjugate

Elvitegravir sodium salt (1.0 moleq) and triphenylmethylphosphonium bromide (1.0 moleq) are added to ethanol with stirring. The salt exchange is allowed to proceed until completion at 25-50° C. The reaction is monitored by TLC. Upon completion, the ethanol is removed under vacuum and the residue taken up in acetonitrile. The insolubles are removed by filtration and the acetonitrile removed under vacuum to afford crude elvitegravir-TPMP conjugate. Purification is attained by column chromatography on silca gel using dichloromethane and ethanol as eluents.

Example 4

Preparation of Levodopa-MitoQ Conjugate

Levodopa sodium salt (1.0 moleq) and MitoQ bromide (1.0 moleq) are added to ethanol-water with stirring. The salt exchange is allowed to proceed until completion at 25-50° C. The reaction is monitored by TLC. Upon completion, the solvent is removed under vacuum and the crude levodopa-MitoQ conjugate purified by column chromatography on silca gel.

Example 5

Preparation of Deoxycholic Acid Conjugates

Deoxycholic Acid-MitoQ Conjugate:

Deoxycholic acid sodium salt (1.0 moleq) and MitoQ bromide (1.0 moleq) are added to ethanol with stirring. The salt exchange is allowed to proceed until completion at 25-50° C. The reaction is monitored by TLC. Upon completion, the ethanol is removed under vacuum and the residue taken up in ether. The insolubles are removed by filtration and the ether removed under vacuum to afford crude elvitegravir-TPMP conjugate. Purification is attained by column chromatography on silca gel using dichloromethane and ethanol as eluents.

Deoxycholic Acid-TPMP Conjugate:

Triphenylmethylphosphonium methyl carbonate (4.26 g; 12 mmol) was dissolved in 50 ml of ethanol and Deoxycholic acid (5 g; 12.7 mmol) was added to it at ambient temperature. The reaction was stirred for 30 minutes and concentrated under vacuum at 50° C. The product was dried under high vacuum at 45° C. to afford 8.5 g of Deoxycholic acid TPMP conjugate.

Example 6

Preparation of Treprostinil Conjugates

Treprostinil-MitoQ Conjugate:

Treprostinil sodium salt (1.0 moleq) and MitoQ bromide (1.0 moleq) are added to ethanol with stirring. The salt exchange is allowed to proceed until completion at 25-50° C. The reaction is monitored by TLC. Upon completion, the solvent is removed under vacuum and the crude treprostinil-MitoQ conjugate purified by column chromatography on silca gel using dichloromethane and ethanol as eluents.

Treprostinil-TPMP Conjugate:

Treprostinil (5.7 g; 14.6 mmol) was dissolved in 57 ml of ethanol and Triphenylmethylphosphonium methyl carbonate (5.14 g; 14.6 mmol) was added to it and stirred at ambient temperature overnight. Gas evolution ($CO_2$) was noted as the reaction progressed. The reaction mixture was concentrated and dried under high vacuum to afford 9.3 g of Treprostinil TPMP conjugate.

Example 7

Preparation of Tamibarotene-MitoQ Conjugate

Tamibarotene sodium salt (1.0 moleq) and MitoQ bromide (1.0 moleq) are added to ethanol with stirring. The salt exchange is allowed to proceed until completion at 25-50° C. The reaction is monitored by TLC. Upon completion, the solvent is removed under vacuum and the crude tam ibarotene-MitoQ conjugate purified by column chromatography on silca gel using dichloromethane and ethanol as eluents.

Example 8

Preparation of Latanoprost Acid-TPMP Conjugate

Latanoprost (7.5 g; 19.2 mmol) was dissolved in 75 ml of ethanol and Triphenylmethylphosphonium methyl carbonate (6.77 g; 19.2 mmol) was added to it and stirred at ambient temperature overnight. Gas evolution ($CO_2$) was noted as the reaction progressed. The reaction mixture was concentrated and dried under high vacuum to afford 13 g of Latanoprost Acid-TPMP conjugate.

Example 9

Preparation of Travoprost Acid-TPMP Conjugate

Travoprost Acid (2.3 g; 5 mmol) was dissolved in 23 ml of ethanol and Triphenylmethylphosphonium methyl carbonate (1.76 g; 5 mmol) was added to it and stirred at ambient temperature overnight. Gas evolution ($CO_2$) was noted as the reaction progressed. The reaction mixture was concentrated and dried under high vacuum to afford 3.2 g of Travoprost Acid-TPMP conjugate.

Example 10

Preparation of L-Thyroxine-TPMP Conjugate

L-Thyroxine (5 g; 5.6 mmol) and Triphenylmethylphosphonium bromide (2 g; 5.6 mmol) in 200 ml of methanol were stirred at ambient temperature for one hour and, subsequently, at 60° C. for two hours. The heat was removed and the reaction mixture concentrated under vacuum. The concentrated reaction product was treated with 200 ml of water. The solids were filtered and washed three times with 20 ml of water. The product was finally dried under vacuum at 45° C. to afford 5 g of L-Thyroxine TPMP conjugate.

Example 11

Preparation of Trans-Retinoic Acid-TPMP Conjugate

Trans-Retinoic acid (4.5 g; 15 mmol) and Triphenylmethylphosphonium methyl carbonate (5.28 g; 15 mmol) were stirred in 20 ml of ethanol at ambient temperature overnight. The reaction mixture was concentrated under vacuum at 60° C. to afford 8.3 g of Retinoic Acid-TPMP conjugate.

Example 12

Preparation of 3-Hydroxybutyric Acid-TPMP Conjugates

Racemic 3-Hydroxybutyric Acid-TPMP Conjugate:
Racemic 3-hydroxybutyric acid (2.5 g; 24 mmol) and Triphenylmethylphosphonium methyl carbonate (8 g; 23 mmol) were stirred in 20 ml of ethanol at ambient temperature overnight. The reaction mixture was concentrated under vacuum at 60° C. to afford 7.9 g of racemic 3-Hydroxybutyric Acid-TPMP conjugate.

(R)-3-Hydroxybutyric Acid-TPMP Conjugate:
(R)-3-hydroxybutyric acid (2.6 g; 25 mmol) and Triphenylmethylphosphonium methyl carbonate (8.8 g; 25 mmol) were stirred in 26 ml of ethanol at ambient temperature overnight. Gas evolution ($CO_2$) was noted as the reaction progressed. The reaction mixture was concentrated under vacuum at 45° C. and the solids triturated with 100 ml of methyl t-butyl ether. The product was dried under high vacuum at 45° C. to afford 8.9 g of (R)-3-Hydroxybutyric Acid-TPMP conjugate.

Example 13

Preparation of Furosemide Conjugates

Furosemide-TPMP Conjugate:
Furosemide (5 g; 15 mmol) was dissolved in 50 ml of ethanol and Triphenylmethylphosphonium methyl carbonate (5.3 g; 15 mmol) was added to it and stirred at ambient temperature overnight. Gas evolution ($CO_2$) was noted as the reaction progressed. The reaction mixture was concentrated under vacuum at 45° C. and the solids triturated with 100 ml of methyl t-butyl ether. The solids were filtered and washed twice with 50 ml of methyl t-butyl ether. The product was dried under high vacuum at 45° C. to afford 9.2 g of Furosemide-TPMP conjugate.

Furosemide-MitoQ Conjugate:
Furosemide (2.73 g; 8.3 mmol) was stirred at ambient temperature with 330 mg of sodium hydroxide and 20 ml of water for two hours at ambient temperature. MitoQ mesylate (5 g; 7.4 mmol) was added along with 50 ml of ethyl acetate and 20 ml of water. The reaction was stirred overnight at ambient temperature under an inert atmosphere and protected from light. The two layers were separated and the organic layer was extracted three times with brine, dried over sodium sulfate, and concentrated under high vacuum at ambient temperature in the dark to afford 6 g of the Furosemide-MitoQ conjugate.

Example 14

Preparation of Sulindac-TPMP Conjugate

Sulindac (4.34 g; 12.1 mmol) was suspended in 86 ml of ethanol and Triphenylmethylphosphonium methyl carbonate (4.28 g; 12.1 mmol) was added to it and stirred at ambient temperature overnight. Gas evolution ($CO_2$) was noted as the reaction progressed. The reaction mixture was concentrated under vacuum at 45° C. and the product dried under high vacuum at 45° C. to afford 7.7 g of Sulindac-TPMP conjugate.

Example 15

Preparation of Indomethacin-TPMP Conjugate

Indomethacin (4.5 g; 12.6 mmol) was suspended in 45 ml of ethanol and Triphenylmethylphosphonium methyl carbonate (4.42 g; 12.6 mmol) was added to it and stirred at ambient temperature overnight. Gas evolution ($CO_2$) was noted as the reaction progressed. The reaction mixture was concentrated under vacuum at 45° C. and the product dried under high vacuum at 45° C. to afford 5.8 g of Indomethacin-TPMP conjugate.

Example 16

Preparation of Captopril-TPMP Conjugate

Captopril (4 g; 18.4 mmol) was dissolved in 40 ml of ethanol and Triphenylmethylphosphonium methyl carbonate (6.49 g; 18.4 mmol) was added to it and stirred at ambient temperature overnight. Gas evolution ($CO_2$) was noted as the reaction progressed. The reaction mixture was concentrated under vacuum at 45° C. and the product dried under high vacuum at 45° C. to afford 7 g of Captopril TPMP conjugate.

Example 17

Preparation of Ascorbic Acid-TPMP Conjugate

Ascorbic acid (3.5 g; 19.9 mmol) was dissolved in 70 ml of water and Triphenylmethylphosphonium methyl carbonate (7 g; 19.9 mmol) was added to it and stirred at ambient temperature overnight. Gas evolution ($CO_2$) was noted as the reaction progressed. The reaction solution was lyophilized to afford 8.8 g of the Ascorbic Acid-TPMP conjugate.

Example 18

Preparation of Diclofenac Conjugates

Diclofenac-TPMP Conjugate:
Diclofenac (6 g; 20.3 mmol) was suspended in 120 ml of ethanol and Triphenylmethylphosphonium methyl carbonate (7.1 g; 20.3 mmol) was added to it and stirred at ambient temperature overnight. Gas evolution ($CO_2$) was noted as the reaction progressed. The reaction mixture was concentrated under vacuum at 35° C. and the product dried under high vacuum at 45° C. to afford 11 g of Diclofenac-TPMP conjugate.

Diclofenac-MitoQ Conjugate:
MitoQ mesylate (2 g; 2.9 mmol) and Diclofenac sodium salt (1 g; 3.1 mmol) were added to flask containing 20 ml of brine, 40 ml of ethyl acetate and 4 ml of water. The reaction was stirred under inert atmosphere and protected from light for approximately 30 minutes. Dichloromethane (10 ml) was added to the reaction mixture and the two layers were separated. The organic layer was washed twice with 10 ml of brine plus 2 ml of water and one time with 10 ml of brine. The organic layer was then dried over sodium sulfate, filtered, and dried under high vacuum in the dark to afford 2.8 g of the Diclofenac-MitoQ conjugate.

Example 19

Preparation of Diflunisal-TPMP Conjugate

Diflunisal (4.25 g; 17 mmol) was dissolved in 85 ml of ethanol and Triphenylmethylphosphonium methyl carbonate (5.98 g; 17 mmol) was added to it and stirred at ambient temperature overnight. Gas evolution ($CO_2$) was noted as the reaction progressed. The reaction mixture was concentrated under vacuum at 50° C. and the product dried under high vacuum at 50° C. to afford 7.5 g of Diflunisal-TPMP conjugate.

Example 20

Preparation of Ciprofloxacin-TPMP Conjugate

Ciprofloxacin (5 g; 15 mmol) was suspended in 50 ml of ethanol and Triphenylmethylphosphonium methyl carbonate (5.05 g; 14.3 mmol) was added to it. The mixture was heated with stirring to 80° C. When the reaction reached 60° C., 10 ml of water was added to it, at which point mild evolution of gas was noted. The reaction was then allowed to proceed overnight at 80° C. The reaction mixture was concentrated under vacuum at 50° C. and the resulting solids triturated with 50 ml of methyl t-butyl ether overnight. The product was filtered and dried under high vacuum at 45° C. to afford 6.8 g of Ciprofloxacin-TPMP conjugate.

Example 21

Preparation of Baclofen-TPMP Conjugate

Baclofen (5 g; 23.4 mmol) was suspended in 50 ml of ethanol and Triphenylmethylphosphonium methyl carbonate (7.83 g; 22.2 mmol) was added to it. The mixture was heated with stirring to 80° C. When the reaction reached ~75° C., evolution of gas was noted. The reaction was then stirred at 80° C. for one hour before it was concentrated under vacuum at 50° C. The product was dried under high vacuum at 45° C. to afford 10.7 g of Baclofen-TPMP conjugate.

Example 22

Preparation of Trans-Ferulic Acid-TPMP Conjugate

Trans-Ferulic acid (3 g; 15.4 mmol) was dissolved in 40 ml of ethanol at ambient temperature and Triphenylmethylphosphonium methyl carbonate (5.4 g; 15.4 mmol) was added to it. The reaction was stirred overnight. The solvent was removed under vacuum and the solid was further dried under high vacuum for a day to afford 6.4 g of the trans-Ferulic Acid-TPMP conjugate.

Example 23

Physicochemical Properties of Phosphonium-Based Ionic Conjugates

The water solubilties and partition coefficients of the PBICs were measured and compared to the values of the therapeutic agent by itself. See Tables 1 and 2, below. To determine the partition coefficient Log $D_{7.4}$ data provided in Table 2, a solution of the compound or conjugate was prepared in aqueous phosphate buffered saline (PBS) at a concentration of 100 micromolar (μM). The PBS solution was shaken with octanol. Thus, in Table 2, Log $D_{7.4}$=Log (concentration in octanol/concentration in aqueous phosphate buffered saline (PBS))=Log[(initial concentration in PBS−final concentration in PBS)/final concentration in PBS], as the concentration in octanol is derived from the loss of compound from the aqueous PBS layer.

The TPMP conjugates increased the parent drug water solubilities multi-fold, whereas the MitoQ conjugates were very hydrophobic (lipophilic). For example, the Diclofenac-MitoQ conjugate was insoluble at a 2 mg/L concentration. Thus, it appears that conjugate hydrophilicity/hydrophobicity can be tailored by adjusting the length of the linker in the phosphonium containing compound.

The Caco-2 Cell Permeabilities were determined using standard Caco-2 culture media (DMEM, 10% FCS, 1% L-Glutamine, 1% PenStrep). Results are shown in Table 3, below.

TABLE 1

Water Solubiltiy of PBICs (in milligram per liter).

| Drug Name | Drug (mg/L) | TPMP Conjugate (mg/L) | MitoQ Conjugate (mg/L) |
|---|---|---|---|
| Travoprost | 7.0 | 1,921,666.7 | |
| Sulindac | 25.0 | 2,532,500.0 | |
| Sulfasalazine | 1.0 | 660.0 | |
| R-3-Hydroxybutyric acid | 444,000.0 | 2,867,500.0 | |
| Indomethacin | 0.9 | 1,700,000.0 | |
| Latanoprost | 8.0 | 2,187,777.8 | |
| Levothyroxine | 0.2 | <400 | |
| Furosemide | 73.1 | 120,000.0 | Insoluble |

TABLE 1-continued

Water Solubiltiy of PBICs (in milligram per liter).

| Drug Name | Drug (mg/L) | TPMP Conjugate (mg/L) | MitoQ Conjugate (mg/L) |
|---|---|---|---|
| Treprostinil | 7.0 | 2,558,000.0 | |
| Retinoic acid | 1,000.0 | 2,624,500.0 | |
| Ibuprofen | 21.0 | 1,978,571.4 | Insoluble |
| 3-hydroxybutyric acid | 444,000.0 | 4,332,500.0 | |
| Baclofen | 700.0 | 13,500.0 | |
| Ciprofloxacin | 30,000.0 | 1,360.0 | |
| Captopril | 160,000.0 | 3,036,666.7 | |
| Deoxycholic acid | 43.6 | 2,518,000.0 | |
| Ascorbic acid | 330.0 | 2,153,333.3 | |
| Diclofenac | 2.4 | 840,000.0 | Insoluble (<2) |
| Diflunisal | 14.5 | 1,518,333.3 | |

TABLE 2

Partition Coefficients of PBICs

| Compound/Conjugate | (Conc. in octanol)/(Conc. in PBS) | $LogD_{7.4}$ | LogP (Reported) |
|---|---|---|---|
| Ibuprofen | | | 3.97 |
| Ibuprofen-TPMP | 13.14 | 1.12 | |
| Ibuprofen-MitoQ | 9.94 | 1.00 | |
| Furosemide | | | 2.03 |
| Furosemide-TPMP | 0.33 | −0.48 | |
| Furosemide-MitoQ | 0.21 | −0.67 | |
| Diclofeac | | | 4.51 |
| Diclofenac-TPMP | 19.88 | 1.30 | |
| Diclofenac-MitoQ | 8.53 | 0.93 | |
| Obeticholic acid | | | 3.5 |
| Obeticholic acid-TPMP | 1,182.39 | 3.07 | |
| Obeticholic acid-MitoQ | 624.00 | 2.80 | |

TABLE 3

Caco-2 Permeability Results

| Compound ID | No Inhibitor | | | With Inhibitor | | |
|---|---|---|---|---|---|---|
| | Mean $P_{app}$ A-B ($10^{-6}$ cm/s) | Mean $P_{app}$ B-A ($10^{-6}$ cm/s) | Mean (B-A/A-B) Efflux Ratio | Mean $P_{app}$ A-B ($10^{-6}$ cm/s) | Mean $P_{app}$ B-A ($10^{-6}$ cm/s) | Mean (B-A/A-B) Efflux Ratio |
| Ibuprofen | 40.5 | 19.0 | 0.469 | 43.3 | 21.5 | 0.496 |
| Ibuprofen-TPMP | 34.2 | 28.8 | 0.842 | 45.0 | 31.9 | 0.709 |
| Ibuprofen-MitoQ | 52.1 | 24.3 | 0.467 | 52.5 | 22.6 | 0.431 |
| Furosemide | 0.155 | 9.95 | 64.4 | 0.211 | 9.62 | 45.5 |
| Furosemide-TPMP | 0.279 | 10.0 | 35.9 | 0.598 | 11.6 | 19.5 |
| Furosemide-MitoQ | 0.314 | 10.3 | 32.7 | 0.324 | 8.80 | 27.2 |
| Diclofenac | 34.5 | 13.5 | 0.391 | 32.8 | 11.2 | 0.340 |
| Diclofenac-TPMP | 15.4 | 8.24 | 0.535 | 35.7 | 11.9 | 0.334 |
| Diclofenac-MitoQ | 34.7 | 2.14 | 0.0618 | 42.1 | 2.50 | 0.0594 |
| Obeticholic acid | 32.6 | 3.23 | 0.0989 | 26.7 | 1.12 | 0.0418 |
| Obeticholic acid-TPMP | 20.5 | 2.11 | 0.103 | 25.1 | 1.01 | 0.0403 |
| Obeticholic acid-MitoQ | 18.9 | 1.65 | 0.0872 | 29.6 | 1.47 | 0.0498 |

Notes:
Permeability Ranking: lower is < 1 × 10 − 6 cm/s; higher is > 1 × 10 − 6 cm/s. An efflux ratio > 2 indicates potential for the compound to be a substrate for Pgp or other active transporter.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A composition comprising an ionic conjugate comprising (a) one or more cationic compounds, wherein each cationic compound comprises a phosphonium group, and (b) an anionic compound comprising a pharmaceutically active compound or a prodrug or derivative thereof; wherein the ionic conjugate has a structure of Formula (I):

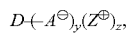

wherein:
D is a residue of a pharmaceutically active compound, or a prodrug or a derivative thereof;
y is an integer;
each A⊖ is an anionic functional moiety, wherein D-(-A⊖)$_y$ comprises a pharmaceutically active compound comprising one or more anionic moieties, an anionic form of a pharmaceutically active compound comprising one or more groups capable of forming an anion, a prodrug of a pharmaceutically active compound comprising one or more anionic moieties, an anionic form of a prodrug of a pharmaceutically active compound comprising one or more groups capable of forming an anion, a derivative of a pharmaceutically active compound wherein the derivative comprises one or more anionic moieties, or an anionic form of a derivative of a pharmaceutically active compound comprising one or more groups capable of forming an anion;

z is an integer; and each $Z^\oplus$ is a compound of the Formula (II):

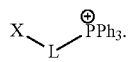

wherein

L is an alkylene group; and

X is a monovalent residue of a compound having antioxidant properties, or a reduced and/or oxidized derivative thereof.

2. The composition of claim 1, wherein X has a structure of one of the Formulas (i), (ii), or (iii):

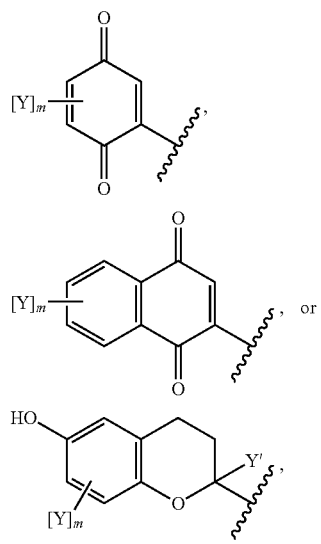

wherein:

m is an integer between 0 and 3;

each Y is independently selected from alkyl and alkoxy; and

Y' is selected from H and alkyl.

3. The composition of claim 1, wherein X has a structure:

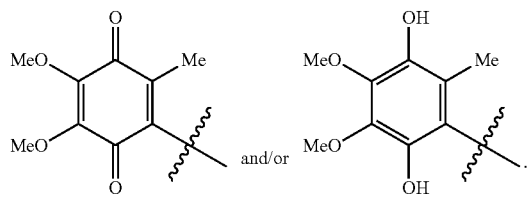 [SMILES: *C1=C(C)C(=O)C(OC)=C(OC)C1=O ; *c1c(C)c(O)c(OC)c(OC)c1O]

4. The composition of claim 1, wherein X has a structure:

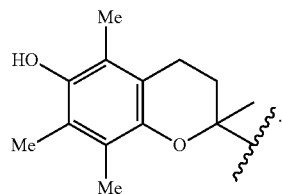 [SMILES: *C1(C)CCc2c(C)c(O)c(C)c(C)c2O1]

5. The composition of claim 1, wherein the pharmaceutically active compound is a compound for treating a disease, disorder, or condition selected from the group consisting of cancer; a disease, disorder, or condition associated with aging; a neurodegenerative disease, disorder or condition; sepsis; a hepatic disease, disorder or condition; a kidney disease, disorder or condition; a cardiovascular disease, disorder, or condition; diabetes or a related condition; Duchenne muscular dystrophy; a pulmonary disease, disorder, or condition; arthritis; inflammation or an inflammatory disease or disorder; an immune system disease, disorder, or condition; an eye disease, disorder, or condition; an infection; pain; a central nervous system disease, disorder or condition; a gastrointestinal disease, disorder or condition; obesity; a sleep disorder; a metabolic disorder; a dermatologic disease, disorder, or condition; a wound, a disease, disorder or condition relating to hair loss; a circulatory disease, disorder, or condition; osteoporosis; blood clotting; organ transplantation; fever; and a nutritional disease, disorder or condition.

6. The composition of claim 1, wherein the pharmaceutically active compound is selected from the group consisting of fexofenadine; dabigatran; tirofiban; sulfasalazine; alitretinoin; azacytidine; bendamustine; bexarotene; bortezomib; chlorambucil; cladribine; clofarabine; cytarabine; decitabine; floxuridine; fludarabine; gemcitabine; isotretinoin; melphalan; mercaptopurine; methotrexate; panobinostat; pazopanib; pemetrexed; raltitrexed; tamibarotene; tretinoin; vinblastine; vincristine; vinflunine; vinorelbine; vorinostat; atorvastatin; rosuvastatin; pravastatin; niacin; fluvastatin; fenofibrate; sumatriptan; baclofen; repaglinide; nateglinide; amphoterisin B; valproate; esmolol; eplerenone; clopidogrel acid; valsartan; trandolapril; telmisartan; ram ipril; quinapril; perindopril; nisoldipine; nimodipine; nicardipine; moexipril; lisinopril; isradipine; fosinopril; eprosartan; enalapril; cerivastatin; captopril; benazepril; amlodipine; a qunilone antibacterial; chloramphenicol; cefditoren; celecoxib; naproxen; ketorolac; ketoprofen; ibuprofen; fenoprofen; diclofenac; penicillamine; pregabalin; gabapentin; levodopa; carbidopa; clorazepic acid; a selective thyroid hormone modulator; a prostaglandin; a prostacyclin; setipiprant; timapiprant; elvitegravir; emtricitabine; oseltamivir; tenofovir; sofosbuvir; zidovudine; zalcitabine; ganciclovir; adefovir; robenacoxib; risedronic acid; tranexamic acid; tenofovir acid; minocycline; ursodeoxycholic acid; chenodeoxycholic acid; hyodeoxycholic acid; obeticholic acid; doxorubicin; a histone deacylase inhibitor; an IP receptor antagonist; a selexipag active metabolite; curcumin; squalamine; pantothenic acid; biotin; and folic acid.

7. The composition of claim 1, wherein the pharmaceutically active compound is selected from the group consisting of prostaglandin acid, prostacyclin acid, or analogs thereof; a statin; a retinoid; an angiotensin receptor blocker; a vasodilator; a dopa decarboxylase inhibitor; an anti-cancer agent; a non-steroidal anti-inflammatory drug (NSAID); a central nervous system (CNS) agent; a cholesterol lowering agent; a diabetes treatment agent; a hypertension treatment agent; a quinolone antibacterial; an osteoporosis drug; and a neuropathic pain agent.

8. The composition of claim 1, wherein the pharmaceutically active compound, prodrug, or derivative thereof comprises one or more anionic moieties derived from a carboxylic acid, a sulfonic acid, a phosphonic acid, a boronic acid, a hydroxamic acid, or a hydroxyl group.

9. A pharmaceutical, veterinary, or cosmetic formulation comprising the composition of claim 1 and a pharmaceutically acceptable carrier.

10. A method of treating a disease, disorder or condition in a subject in need of treatment thereof, the method comprising administering to the subject a composition of claim 1.

11. The method of claim 10, wherein the disease, disorder or condition is selected from the group consisting of cancer; a disease, disorder, or condition associated with aging; a neurodegenerative disease, disorder or condition; sepsis; a kidney disease, disorder or condition; a hepatic disease, disorder or condition; a cardiovascular disease, disorder, or condition; diabetes or a related condition; Duchenne muscular dystrophy; a pulmonary disease, disorder, or condition; arthritis; inflammation or an inflammatory disease or disorder; an immune system disease, disorder, or condition; an eye disease, disorder, or condition; an infection; pain; a central nervous system disease, disorder or condition; a gastrointestinal disease, disorder or condition; obesity; a sleep disorder; a metabolic disorder; a dermatologic disease, disorder, or condition; a wound, disease, disorder or condition relating to hair loss; a circulatory disease, disorder, or condition; osteoporosis; blood clotting; organ transplantation; fever; and a nutritional disease, disorder or condition.

12. The method of claim 10, wherein the administrating is via a route selected from the group consisting of oral, intravenous, subcutaneous, intramuscular, transdermal, topical, sublingual, subcutaneous, buccal, rectal, intraperitoneal, intrathecal, intravitreal, intraocular, aerosol, and nasal.

13. The composition of claim 2, wherein X has a structure:

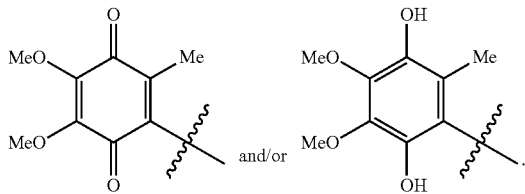 [SMILES: *C1=C(C)C(=O)C(OC)=C(OC)C1=O ; *c1c(C)c(O)c(OC)c(OC)c1O]

14. The composition of claim 2, wherein X has a structure:

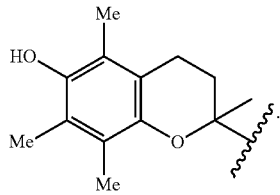 [SMILES: *C1(C)CCc2c(C)c(O)c(C)c(C)c2O1]

15. A method of treating a disease, disorder or condition in a subject in need of treatment thereof, the method comprising administering to the subject a pharmaceutical, veterinary, or cosmetic formulation of claim 9.

16. The method of claim 11, wherein the administrating is via a route selected from the group consisting of oral, intravenous, subcutaneous, intramuscular, transdermal, topical, sublingual, subcutaneous, buccal, rectal, intraperitoneal, intrathecal, intravitreal, intraocular, aerosol, and nasal.

17. The composition of claim 1, wherein D is a mono- or divalent residue of a pharmaceutically active compound, or a prodrug or a derivative thereof.

18. The composition of claim 1, wherein y is 1 or 2.

19. The composition of claim 1, wherein each $A^{\ominus}$ is the anionic form of a moiety selected from the group consisting of a carboxylic acid, a sulfonic acid, a phosphonic acid, an amidine, a boronic acid, a hydroxamic acid, a thiol, a phenol, and a hydroxyl.

20. The composition of claim 1, wherein z is 1 or 2.

21. The composition of claim 1, wherein L is a saturated or unsaturated, substituted or unsubstituted C1-C15 alkylene group.

22. The composition of claim 1, wherein X is a monovalent residue of a compound having antioxidant properties, or a reduced and/or oxidized derivative thereof, wherein the compound comprising antioxidant properties is selected from the group consisting of a quinone, a quinol, a benzoquinone, a benzoquinol, a plastoquinone, a plastoquinol, a chroman, a chromene, a chromone, and ascorbic acid.

23. The composition of claim 2, wherein m is 1, 2, or 3.

24. The composition of claim 8, wherein each of the one or more anionic moieties is derived from a carboxylic acid.

* * * * *